(12) United States Patent
Benkirane-Jessel et al.

(10) Patent No.: US 10,034,737 B2
(45) Date of Patent: Jul. 31, 2018

(54) NANO-RESERVOIRS TECHNOLOGY FOR USE IN BONE AND/OR CARTILAGE REGENERATION

(75) Inventors: Nadia Benkirane-Jessel, Strasbourg (FR); Didier Mainard, Nancy (FR); Carlos Mendoza Palomares, Strasbourg (FR)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 132 days.

(21) Appl. No.: 14/000,631

(22) PCT Filed: Feb. 22, 2012

(86) PCT No.: PCT/EP2012/052976
§ 371 (c)(1),
(2), (4) Date: Aug. 21, 2013

(87) PCT Pub. No.: WO2012/113812
PCT Pub. Date: Aug. 30, 2012

(65) Prior Publication Data
US 2013/0325144 A1 Dec. 5, 2013

(30) Foreign Application Priority Data
Feb. 22, 2011 (EP) .................... 11305182

(51) Int. Cl.
| A61F 2/02 | (2006.01) |
| A61L 27/24 | (2006.01) |
| A61L 27/54 | (2006.01) |
| A61L 27/18 | (2006.01) |
| A61L 27/34 | (2006.01) |
| A61L 27/38 | (2006.01) |

(52) U.S. Cl.
CPC ............. *A61F 2/02* (2013.01); *A61L 27/18* (2013.01); *A61L 27/24* (2013.01); *A61L 27/34* (2013.01); *A61L 27/3817* (2013.01); *A61L 27/3821* (2013.01); *A61L 27/54* (2013.01); *A61L 2300/414* (2013.01); *A61L 2400/12* (2013.01); *A61L 2420/08* (2013.01)

(58) Field of Classification Search
None
See application file for complete search history.

(56) References Cited

U.S. PATENT DOCUMENTS

2007/0154513 A1   7/2007  Atanasoka

FOREIGN PATENT DOCUMENTS

| JP | 2009-39139 | 2/2009 |
| JP | 2010535605 | 11/2010 |
| WO | 2005/089825 A2 | 9/2005 |
| WO | WO 2005/089825 | * 9/2005 |
| WO | 2010/086406 A1 | 8/2010 |

OTHER PUBLICATIONS

Li e al., "Coating Electrospun Poly(ε-caprolacone) Fibers with Gelatin and Calcium Phosphate and Their Use as Biomeimetic Scaffolds for Bone Tissue Engineering", Langmuir, 24(24), 2008, pp. 14145-14150.*
Li et al., "Coating Electrospun Poly(E-caprolactone) Fibers wtih Gelatin and Calcium Phosphate and Their Use as Biomimetic Scaffolds for Bone Tissue Engineering", Langmuir, 24, 2009, pp. 14145-14150.*
Maretschek et al., "Electrospun biodegradable nanofiber nonwovens for controlled release of proteins", Journal of Controlled Release, 127, 2009, pp. 180-187.*
Yilgor et al., "Effect of scaffold architecture and BMP-2/BMP-7 delivery on in vitro bone regeneration", J. Mater Sci: Mater Med, 21, 2010, pp. 2999-3008.*
Almodovar et al., "Coating Electrospun Chitosan Nanofibers with Polyelectrolyte Multilayers Using the Polysaccharides Heparin and N,N,N-Trimethyl Chitosan", Macromolecular Bioscience, Oct. 25, 2010, pp. 72-76, vol. 11, No. 1.
Xiaoran et al., "Coating Electrospun Poly([epsilon]-caprolactone) Fibers with Felatin and Calcium Phosphate and Their Use as Biomimetic Scaffolds for Bone Tissue Engineering", Langmuir, Dec. 16, 2008, pp. 14145-14150, vol. 24, No. 24.
Crouzier et al. Layer-By-Layer Films as a Biomimetic Reservoir for rhBMP-2 Delivery: Controlled Differentiation of Myoblasts to Osteoblasts, Small 2009; 5(5):598-608.

* cited by examiner

*Primary Examiner* — Melissa L Fisher
(74) *Attorney, Agent, or Firm* — W&C IP

(57) ABSTRACT

The present invention concerns a biomaterial comprising a nanofibrous scaffold made of polymers, such as poly(ε-caprolactone) or collagen, coated with at least one layer pair consisting of a layer of polyanions and a layer of polycations, wherein said at least one layer pair incorporates a therapeutic molecule such as a growth factor. The biomaterial may optionally comprise living cells such as osteoblasts and/or chondrocytes.

22 Claims, 9 Drawing Sheets

NANO-RESERVOIRS TECHNOLOGY FOR USE IN BONE AND/OR CARTILAGE REGENERATION

The present invention concerns a biomaterial comprising a nanofibrous scaffold made of polymers, such as poly(ε-caprolactone) or collagen, coated with at least one layer pair consisting of a layer of polyanions and a layer of polycations, wherein said at least one layer pair incorporates a therapeutic molecule such as a growth factor. The biomaterial may optionally comprise living cells such as osteoblasts and/or chondrocytes.

Aging is a global phenomenon. The world's elderly population aged 60 and over is the fastest growing age group. This is a positive sign of improving health. Nevertheless, along with it come new health challenges. The opportunities for nanomedicine to maintain the health of this aging population are limitless. For successful regenerative medicine, tissue-engineering strategies based on new nanostructured and living implants become crucial. Osteoarthritis, as a classic age-related disease (joint pain and articular cartilage degeneration), is an obvious major focus of applied research in nanomedicine.

In the field of bone and/or cartilage repair, the use of nanostructured biomaterials appears to be attractive. The attractiveness of nanotechnology applications lies in the unique characteristics and phenomena that manifest due to their small size. Engineering materials on this nano-scale allow for novel medical therapies such as designing nanoparticle-based drugs that target cells with improved specificity, resulting in decreased side effects for patients. Other advances are being made in nanostructured biomaterials for use in surgical implantations that are less invasive, leading to shorter recovery times and decreased risk of postoperative infections or other complications. Such innovations will improve the quality of life, extend life expectancies, and could reduce the overall cost of healthcare. Biomaterials play central roles in modern strategies in regenerative medicine and tissue engineering as designable biophysical and biochemical milieus that direct cellular behavior and function.

Tissue engineering is an interdisciplinary field that has attempted to utilize a variety of processing methods with synthetic and natural polymers to fabricate scaffolds for the regeneration of tissues and organs. The study of structure-function relationships in both normal and pathological tissues has been coupled with the development of biologically active substitutes or engineered materials.

The materials focus is limited to 3-D applications and is on emerging classes of polymeric biomimetic materials, such as nanofibrillar, supramolecular materials formed by self-assembly processes, and matrices presenting individual or multiple biochemical extra-cellular matrix (ECM)-derived signals. The guidance provided by biomaterials may facilitate restoration of structure and function of damaged or dysfunctional tissues. Such materials should provide provisional 3-D support to interact with cells to control their function, guiding the spatially and temporally complex multicellular processes of tissue formation and regeneration (Dvir et al. 2011 Nature Nanotechnology 6:13-22).

Current methods aimed at repairing full-thickness cartilage defects include marrow-stimulation techniques (MST), such as subchondral drilling, abrasion, arthroplasty and microfracture. For example, MST attempts to stimulate filling of a cartilage defect with reparative tissue resulting from perforation of the subchondral bone. There are, however, concerns over the durability of the repair tissue and hence the clinical outcome, especially in defects that are larger than 2-4 cm2 and located in areas other than the femoral condyles (Kreuz et al. 2006 Osteoarthritis Cartilage 14:1119-1125). These limited techniques are generally not sufficient to restore a durable cartilage repair. It is becoming apparent that without a healthy subchondral bed, the entire osteochondral unit is likely to fail.

Therefore, the future of articular cartilage repair depends on the development of advanced implants that will allow the replacement of the entire osteochondral unit. Recently, the development of advanced materials based on ECM analogues has become a major focus of applied research in regenerative medicine. Until now, different studies have focused on either bone or cartilage regeneration and never on the restoration of the entire osteo-chondral unit.

Li et al. (2005 Biomaterials. 26:599-609) and Savarino et al. (2007 Biomaterials. 28:3101-9) describe nanofibrous scaffolds made of biodegradable polymers comprising either mesenchymal stem cells, or bone marrow stromal cells. However, these biomaterials, which are based solely on the use of living cells, do not permit sustained release of a given, specific therapeutic molecule. In addition, these biomaterials necessarily comprise living cells, which makes their use difficult, in particular when small bone defects are to be treated. Moreover, the biomaterial disclosed in Savarino et al. (2007 Biomaterials. 28:3101-9) is based on the use of recombinant mesenchymal stem cells engineered to express BMP4. Such kind of cells cannot be used in the clinics.

Medtronic commercializes a nanofibrous scaffold named InductOS®, which is a collagen matrix soaked in BMP2. However, InductOS® does not present slow release kinetics for BMP2, such slow release kinetics being recognized as a critical requirement for combination implants.

There is thus a need in the art for biomaterials allowing efficient bone and/or cartilage repair, and in particular of biomaterials allowing restoration of the entire osteo-chondral unit. Ideally, these biomaterials should allow slow and controlled release of growth factors playing a role in bone and/or cartilage repair.

DESCRIPTION OF THE INVENTION

The inventors report here the first demonstration of an active living nanostructured hybrid membrane, incorporating smart nano-reservoirs of growth factors, for subchondral bone regeneration. The biomaterials according to the invention advantageously create nano-reservoirs of therapeutic molecules for slow and controlled release over the period of tissue re-growth.

More specifically, the inventors have found that nanofibrous scaffolds can be functionalized through coating with polyelectrolyte multilayers incorporating a growth factor (see e.g. FIGS. 3, 6 and 7). In addition, living cells may be deposited on these coated nanofibrous scaffold.

It has further been demonstrated that such functionalized nanofibrous scaffolds are capable of efficiently inducing bone regeneration in vivo (see e.g. FIG. 5).

Biomaterials According to the Invention

The present invention provides a biomaterial comprising:
a) a nanofibrous scaffold made of biodegradable polymers, coated with at least one layer pair consisting of a layer of polyanions and a layer of polycations, wherein said at least one layer pair incorporates a therapeutic molecule such as a growth factor; and, optionally,
b) living cells.

These biomaterials are characterized in that the nanofibrous scaffold is coated with at least one layer pair consisting of a layer of polyanions and a layer of polycations, wherein said at least one layer pair incorporates a therapeutic molecule such as a growth factor. In a preferred embodiment, said layer pair is in the form of or comprised within multilayered droplet. According to one embodiment, the nanofibrous scaffold is multilayered droplet coated.

By "biomaterial" is meant any material suitable for use in vivo in mammals, in particular in human patients. More specifically, the biomaterials according to the invention are suitable for use as implants.

The biomaterial according to the invention comprises a nanofibrous scaffold made of polymers. Said polymers may either be synthetic or natural. Said nanofibrous scaffold is preferably porous, or comprises at least one porous side or part. The polymers are preferably biodegradable. However, nanofibrous scaffolds made of non-biodegradable polymers are also contemplated herein since such scaffolds are useful e.g. when carrying out a spinal fusion, in replacement of a prosthesis, or as a bone defect filling material. Preferably, a nanofibrous scaffold is made of nanofibers, notably synthetic or natural nanofibers.

Nanofibrous scaffolds are based on nanofibers typically having a diameter of about 50 to about 1000 nm, preferably of about 50 to about 500 nm or of about 100 to about 1000 nm, and which form a material with a high porosity and an interconnected pore structure. Such material is particularly suitable as a scaffold structure notably because of its high specific surface area.

Nanofibrous scaffolds according to the invention may have a thickness of at least about 50 micron, 75, 100, 150, 170, 200, 250, 300, 350, 500, 600, 800, 1000, 1500 micron and/or less than 20 mm, 15, 10, 9, 8, 5, 4, 2, 1, 0.8, 0.6, 0.5, 0.4, 0.3, 0.2, 0.1, 0.09, 0.08 mm.

As used throughout the present specification, the term "nanofibrous scaffold" refers to a matrix that is capable of mimicking the natural properties of a tissue (e.g. of bone and/or cartilage) while providing a temporary scaffold for tissue regeneration. That is to say, the nanofibrous scaffold not only mimics the three-dimensional structure of a tissue, but also facilitates adhesion and spreading of cells.

In the frame of the present invention, the nanofibrous scaffold preferably mimics the three-dimensional structure of bone and/or cartilage. The nanofibrous scaffold comprises nanofibers. According to the invention, the nanofibrous scaffold is functionalized with a therapeutic molecule (preferably a growth factor) and optionally with living cells, and thus also serves as a reservoir for the therapeutic molecule and, when living cells are present, as a cell delivery vehicle.

Nanofibrous scaffolds suitable for use as implants are well-known to the skilled in the art. For example, Swieszkowski et al. (2007 Biomol Eng. 24:489-95) discloses several nanofibrous scaffolds suitable for use as implants in the frame of bone and/or cartilage regeneration. These nanofibrous scaffolds made of biodegradable polymers can for instance be made of poly(ε-caprolactone), collagen, fibrin, poly(lactic acid), poly(glycolic acid), poly(ethylene glycol)-terephtalate, poly(butylenes terephtalate), or co-polymers thereof. The nanofibrous scaffold can also be made of polymers such as collagen, hyaluronic acid, hydroxylapatite, chondroitine sulfate, chitosan, and mixtures thereof.

In a preferred embodiment, the nanofibrous scaffold is made of and/or consists of poly(ε-caprolactone) (PCL). In the frame of the present invention, the PCL is preferably electrospun. Nanofibrous scaffolds made of electrospun PCL can for example be obtained as described in the two first paragraphs of Example 1, or as described in Li et al. (2005 Biomaterials. 26:599-609) or in Savarino et al. (2007 Biomaterials. 28:3101-9).

In another preferred embodiment, the nanofibrous scaffold is made of and/or consists of collagen. Collagen is a natural polymer that can for example be obtained from pig. Nanofibrous scaffolds made of collagen are commonly used as implants, and include e.g. the Bio-Gide® resorbable collagen membrane commercialized by Geistlich Pharma AG (Germany).

In the frame of the present invention, the nanofibrous scaffold is functionalized with a therapeutic molecule, allowing sustained release of said therapeutic molecule at the site of implantation of the biomaterial according to the invention.

As used throughout the present specification, the term "therapeutic molecule" refers to any molecule intended to treat or prevent a disease. It may for example correspond to a drug for which a marketing approval has been issued (e.g. by the European Medicines Agency (EMA) or by the U.S. Food and Drug Administration (FDA)), or to a candidate drug undergoing clinical or pre-clinical trials. The therapeutic molecule may for example correspond to a polypeptide (including recombinant proteins, antibodies and peptides), a nucleic acid (including RNA and DNA molecules), a chemical molecule (e.g. a small molecule), or a sugar (e.g. a lipopolysaccharide).

In a preferred embodiment according to the invention, the therapeutic molecule is a growth factor such as, e.g., a bone morphogenetic protein (BMP), a transforming growth factor (TGF), a fibroblast growth factor (FGF), or a nucleic acid coding therefore.

When the biomaterial according to the invention is used for bone and/or cartilage regeneration, said growth factor is most preferably selected from the group consisting of bone morphogenetic protein 2 (BMP2, the sequence of human BMP2 being shown as SEQ ID NO: 1), bone morphogenetic protein 4 (BMP4), bone morphogenetic protein 7 (BMP7) the sequence of human BMP7 being shown as SEQ ID NO: 2, fibroblast growth factor 1 (FGF1), fibroblast growth factor 2 (FGF2), fibroblast growth factor 4 (FGF4), fibroblast growth factor 8 (FGF8), fibroblast growth factor 9 (FGF9) and fibroblast growth factor 18 (FGF18).

The inventors have surprisingly found that it is possible to coat the nanofibrous scaffold with at least one layer pair consisting of:
  a layer of polyanions; and
  a layer of polycations,
wherein said at least one layer pair incorporates the therapeutic molecule.

According to some embodiments, the nanofibrous scaffold is multilayered droplet coated. The nanofibrous scaffold is preferably not film coated.

The coating according to the invention is preferably, irregularly spread over the nanofiber surface.

More specifically, the nanofibrous scaffold according to the invention is coated, on a layer-by-layer basis, with layers that are alternatively negatively or positively charged. At least one of these layers incorporates and/or consists of the therapeutic molecule. For example, FIG. 3 shows nanofibrous scaffolds coated with one to six layer pairs each consisting of a layer of polyanions (namely BMP2, which is negatively charged), and a layer of polycations (namely DGL$^{G5}$, which is positively charged). As can be seen on FIGS. 3 and 9, these layers form "multilayered droplet" on the surface of the nanofibrous scaffold. This coating allows functionalizing the nanofibrous scaffold with a therapeutic molecule in such a way as to create nano-reservoirs of therapeutic molecules. The term "multilayered droplet" refers to droplets or patches composed of at least one layer pair consisting of a layer of polyanions and a layer of polycations. Said droplets can present different shapes: circle shaped, oval-shaped or scale shaped. Preferably said droplets have a size of 10 to 150 nm, more preferably 15 to 100 nm, even more preferably 25 to 50 nm.

According to the invention, the term "multilayered droplet coating" refers to a coating of droplets or patches disposed at the surface of the nanofiber and obtained by layer-by-layer (LbL) deposition of oppositely charged molecules multilayered droplet. The term "multilayered droplet coating" further refers to an interrupted coating of the nanofibers, i.e. a coating that is not in the form of a continuous film along the surface of the nanofibers. The multilayer droplet coating may be characterized by its irregular shape and/or by the fact that it does not cover the totality of the surface of the nanofiber, in such a way that at least a part of the surface of the nanofiber is not coated. The multilayer droplet coating of the invention may be contrasted with a film coating having a smooth surface and covering the totality of the nanofiber surface (see FIG. 9).

The building of the coating is based on the layer-by-layer (LbL) deposition of oppositely charged molecules. That is to say, the coating of the nanofibrous scaffold is made in the same manner as is made a polyelectrolyte multilayered film. The biomaterial according to the invention thus comprises polyelectrolyte multilayers, in the form of numerous multilayered droplet, on the surface of the nanofibrous scaffold (see FIG. 3).

In contrast to a film coating that covers all the nanofiber surface (see FIG. 9C), the multilayered droplet coating according to the invention preferably only partially covers the nanofiber surface (FIGS. 9A and 9B). The coating according to the invention is applied layer by layer (LbL), the excess amount of polyanions or polycations is removed at each step with rinsing steps between consecutive adsorption steps. Due to the repartition of the surface charges of the polymer constituting the nanofiber, the first layer of polyanions or polycations form small droplets or patches adsorbed along the surface of the nanofibers. At each step of the polyanions or polycations polymer application, each droplet is covered by a new layer of polyanions or polycations polymer. The coating process is stopped when the multilayered droplet coating is observed and before a film coating. The multilayered droplet coating provides advantageous characteristics to the nanofiber, which are not observed with a film coating. When the film coating is obtained, the multilayered droplet can not be obtained any more along the surface of the coated nanofiber.

The first advantage of the multilayered droplet coating compared with the film coating or the uncoated nanofiber is its irregular surface (see FIGS. 9A and 9B). This irregular shape improves the adherence of the cells to the nanofibrous scaffold. The inventors show a reduction of time of colonization of the matrix by the cells. Indeed, the matrix according the invention accelerates the tissue regeneration process. Moreover, this irregular shape provides an increase of the surface of contact between the coating and the cells, optimizing the exchanges between the coating and the cells. Consequently, a small concentration of therapeutic molecule is needed for observing a better stimulation of cell growth.

In addition, the coating of the invention uses fewer polyanions and polycations layers than the film coating. A reduced number of layers are thus needed to obtain the multilayered droplet coating.

The corollary is that a fewer quantity of therapeutic molecule can be applied on the nanofibrous scaffold. Indeed, with the membrane of the invention, the therapeutic molecule can be applied at a reduced level (up to 2600 times less than the prior art membranes). It is well known that overdosing of the therapeutic molecule increases the occurrence of side effects. By way of example, overdosing of BMP-2 is known to be responsible of cell lysis and immunization of the patient against BMP-2, reducing strongly the success of the tissue regeneration process. The inventors have shown that the time of tissue regeneration can be greatly improved using fewer polyanions and polycations layers and less therapeutic molecule than the previous art.

By "nanofibers" is meant natural or polymeric filaments which constitute the nanofibrous scaffold.

As further used herein, the term "polyelectrolyte multilayers" notably encompasses the multilayered droplet that coat the nanofibrous scaffold according to the invention.

In the frame of the present specification, the term "polyelectrolyte" designates compounds that bear several electrolyte groups, in particular polymers whose repeating units carry electrolyte groups. The groups will dissociate in aqueous solutions, giving rise to polyanions or polycations, as the case may be, and making the polymers charged.

The polyelectrolyte multilayers that coat the nanofibrous scaffold are composed of at least one layer pair consisting of a layer of polyanions and of a layer of polycations. They may for example comprise 1, 2, 3, 4, 5, 6, 7, 8, 9, 10, 11, 12, 13, 14, 15 or more layer pairs. Preferably, it comprises from 3 to 12 layer pairs.

Therapeutic molecules can be incorporated into polyelectrolyte multilayers, as described, e.g., in WO 02/085423, WO 2006/079928, Lynn (2006 Soft Matter 2:269-273), Decher (1997 Science 277:1232-1237) and Jessel et al. (2003 Advanced Materials 15:692-695).

Polyelectrolyte multilayers, and in particular multilayered droplet as described herein, can easily be obtained by the alternate dipping of the nanofibrous scaffold in polyanion and polycation solutions, as described in detail in the Examples and in the paragraph entitled "Methods for producing biomaterials according to the invention".

As apparent to the skilled in the art, the only requirement for the choice of the polyanions and polycations is the charge of the molecule, i.e., the polyanion shall be negatively charged and the polycation shall be positively charged. The polyanions and polycations according to the invention may correspond to any type of molecule, such as e.g. a polypeptide (optionally chemically modified) or a polysaccharide (including cyclodextrins, chitosan, etc.).

Molecules that are commonly used as polycations when building polyelectrolyte multilayers include, e.g., poly(lysine) polypeptides (PLL), covalently-coupled cyclodextrin-poly(lysine) (PLL-CDs), poly(arginine) polypeptides, poly(histidine) polypeptides, poly(ornithine) polypeptides, Dendri-Graft Poly-lysines (e.g. Dendri-Graft Poly-L-lysines) and chitosan. Molecules that are commonly used as polyanions when building polyelectrolyte multilayers include, e.g., poly(glutamic acid) polypeptides (PGA) and poly(aspartic acid) polypeptides. These polyanions and polycations can be used in the frame of the present invention.

The polyelectrolyte multilayers that coat the nanofibrous scaffold necessarily incorporate a therapeutic molecule.

When the therapeutic molecule to be incorporated to the biomaterial according to the invention is charged, said therapeutic molecule may be used as a polyanion or as a polycation when building the polyelectrolyte multilayers. When the therapeutic molecule is not charged, or not sufficiently charged, it may be covalently linked with a polyanion or a polycation (e.g. one of those listed above) in order to build the polyelectrolyte multilayers.

In a specific embodiment, the polyelectrolyte multilayers comprises or consists of at least 1, 2, 3, 4, 5, 6, 7, 8, 9, 10, 11, 12, 13, 14, 15 or more layer pairs, each layer pair consisting of:
a layer of polyanions comprising or consisting of the therapeutic molecule (such as e.g. a polypeptide, in particular a growth factor); and
a layer of polycations comprising or consisting of chitosan or of a polymer of lysines (such as e.g. a poly (lysine) polypeptide (PLL) or a Dendri-Graft poly-lysine (DGLs)).

In a specific embodiment according to the invention, the layer of polycations comprises or consists of a polymer of lysines being Dendri-Graft poly-lysines (DGLs). Methods for obtaining DGLs are known to the skilled in the art. DGLs can for example be prepared as described in Colletet et al. (2010 Chem. Eur. J. 16:2309-2316). According to the invention, the DGLs can be of any generation, e.g. be of first, second, third, fourth or fifth generation.

In a specific embodiment, the polyelectrolyte multilayers is one of those described in the examples, i.e. $(DGL^{G5}\text{-}BMP2)_1$, $(DGL^{G5}\text{-}BMP2)_2$, $(DGL^{G5}\text{-}BMP2)_3$, $(DGL^{G5}\text{-}BMP2)_4$, $(DGL^{G5}\text{-}BMP2)_5$ or $(DGL^{G5}\text{-}BMP2)_6$, $(PLL\text{-}BMP2)_1$; 2: $(PLL\text{-}BMP2)_2$, $(PLL\text{-}BMP2)_3$, $(PLL\text{-}BMP2)_4$, $(PLL\text{-}BMP2)_5$, $(PLL\text{-}BMP2)_6$, $(Chi\text{-}BMP2)_1$, $(Chi\text{-}BMP2)_2$, $(Chi\text{-}BMP2)_3$, $(Chi\text{-}BMP2)_4$, $(Chi\text{-}BMP2)_5$ or $(Chi\text{-}BMP2)_6$. "$DGL^{G5}$" stands for fifth-generation Dendri-Graft Poly-L-lysines. "BMP2" stands for the bone morphogenetic protein 2 of SEQ ID NO: 1. "PLL" stands for poly(lysine) polypeptides. "Chi" stands for chitosan. "$_n$" indicates the number of layer pairs.

In the context of the present invention, the nanofibrous scaffold may further be functionalized with living cells. Indeed, implanting living cells is a promising solution to tissue or organ repair.

In the context of bone and/or cartilage regeneration, said living cells may for example comprise or consist of osteoblasts, chondrocytes, stem cells (e.g. mesenchymal stem cells), bone marrow stromal cells, or a mixture thereof. Preferably, said living cells comprise or consist of osteoblasts, chondrocytes, or a mixture thereof. In a specific embodiment, embryonic stem cells may be excluded from the living cells according to the invention.

Said living cells are preferably human cells, and most preferably autologous cells (i.e. cells that are obtained from the patient to be treated).

Said living cells are preferably obtained by Induced pluripotent stem cells (iPSCs) technology.

In a specific embodiment, said living cells are comprised within a hydrogel (e.g. an alginate hydrogel or a collagen hydrogel) that is deposited on said coated nanofibrous scaffold. In other terms, the biomaterial according to the invention may comprise, in addition to the coated nanofibrous scaffold, a hydrogel comprising living cells.

Hydrogels are well-known to the skilled in the art. A collagen hydrogel may for example be prepared by mixing collagen (e.g. 3 mL of Rat Tail Type-I Collagen) with a medium containing 10% FBS (e.g. 5.5. mL) and with a 0.1 M NaOH solution (e.g. 0.5. mL). An alginate hydrogel may for example be a mixture of alginate and hyaluronic acid (e.g. a alginate:hyaluronic acid solution (4:1), which may be prepared in a 0.15 M NaCl solution at pH 7.4).

In a preferred embodiment according to the invention, the biomaterial according to the invention comprises or consists of:
the nanofibrous scaffold made of polymers that is coated with at least one layer pair consisting of a layer of polyanions and a layer of polycations; and
osteoblasts that are optionally comprised within a collagen hydrogel (deposited on said coated nanofibrous scaffold).

In another preferred embodiment according to the invention, the biomaterial according to the invention comprises or consists of:
the nanofibrous scaffold made of polymers that is coated with at least one layer pair consisting of a layer of polyanions and a layer of polycations;
osteoblasts that are optionally comprised within a collagen hydrogel (deposited on said coated nanofibrous scaffold); and
chondrocytes comprised within an alginate hydrogel (deposited on said coated nanofibrous scaffold).

In still another preferred embodiment according to the invention, the biomaterial according to the invention comprises or consists of:
the nanofibrous scaffold made of polymers that is coated with at least one layer pair consisting of a layer of polyanions and a layer of polycations;
chondrocytes comprised within an alginate hydrogel (deposited on said coated nanofibrous scaffold).

In still another preferred embodiment according to the invention, the biomaterial according to the invention does not comprise living cells. More specifically, it may simply consist of the nanofibrous scaffold made of polymers that is coated with at least one layer pair consisting of a layer of polyanions and a layer of polycations.

In specific embodiments, the biomaterial according to the invention is:
a) a nanofibrous scaffold made of electrospun poly(ε-caprolactone), coated with one, two, three, four, five or six layer pair(s) each consisting of a layer of a growth factor (e.g. BMP2) and a layer of a polymer of lysines (e.g. PLL or DGLs), and, optionally, osteoblasts (e.g. comprised within a hydrogel such as a collagen hydrogel) and/or chondrocytes (e.g. comprised within a hydrogel such as an alginate hydrogel);
b) a nanofibrous scaffold made of collagen, coated with one, two, three, four, five or six layer pair(s) each consisting of a layer of a growth factor (e.g. BMP2) and a layer of a polymer of lysines (e.g. PLL or DGLs), and, optionally, osteoblasts (e.g. comprised within a hydrogel such as a collagen hydrogel) and/or chondrocytes (e.g. comprised within a hydrogel such as an alginate hydrogel); or
c) the nanofibrous scaffold of (a) or (b), wherein the polymer of lysines is replaced with chitosan.

The inventors have shown that (i) a nanofibrous scaffold implant enriched in therapeutic molecules and having a controlled size and thickness can be produced, (ii) bone formation and articular cartilage repair can be induced in vitro.

For articular cartilage repair, it is becoming apparent that without support from an intact subchondral bed, any treatment of the surface chondral lesion is likely to fail. The treatment goal for large chondral or osteochondral defects should be to restore the physiological properties of the entire osteochondral unit, aiming to achieve a more predictable repair tissue that closely resembles native articular surface and remains durable over time. The inventors report here the first demonstration of subchondral bone regeneration using a strategy based on a synthetic nanostructured membrane. This electrospun membrane is manufactured using an FDA approved polymer and functionalized with nano-reservoirs of a therapeutic molecule such as a growth factor (BMP2).

The European and American authorities have already approved the use of BMP-2 for bone regeneration applications. For example, Medtronic offers InductOS® which is a basic collagen matrix soaked in BMP-2. The efficacy of this kind of combination device is dependent on slow release kinetics for BMPs. This criterion is recognized as the critical, most challenging requirement for combination implants. For efficient bone regeneration, the target cells require a reliable and continuous exposure to growth factors over an extended period of time, until the induction of new bone or subchondral bone. The currently available devices are unsophisticated in this respect. In contrast, the inventors proposed medical device, with cell-contact dependent delivery from nano-reservoirs, is designed specifically for sustained availability of BMP-2. This strategy aims at a considerable enhancement of therapeutic efficacy compared to current simplistic approaches. Noteworthy, it is also economically valuable, as reduced amounts of therapeutic molecule are needed for the coating treatment.

Degradation of therapeutic molecule often occurs rapidly in aqueous solution and this is the case for BMP-2. With current systems using collagen matrices soaked with the growth factor, this problem is addressed by overdosing, which may induce adverse side effects. The inventors provide an advantageous approach that lies in the nano-immobilization and the protection of therapeutic molecules. The nanostructured scaffold is produced using a special coating process that entraps therapeutic molecules into deposits onto the scaffold nanofibers. Encapsulated by polymers, the therapeutic molecule is protected and stabilized. Once cells come into contact with the nano-reservoirs (the multilayered droplet), cellular enzymes degrade the polymer coating and the therapeutic molecule becomes available. As the cells grow, divide and infiltrate deeper into the porous structure of the membrane they provoke a slow and progressive release of the therapeutic molecule that, in turn, induce a physiological effect such as stimulates further proliferation of the cells when the therapeutic molecule is a growth factor. This smart "cell-dependent" nano-reservoirs permits a sustained release of the therapeutic molecule.

With this strategy it should be possible to fabricate at reduced cost a combination cell-therapy implant capable of robust and durable cartilage or bone repair in large defects. In addition, the possibility to continue the LbL buildup over the desired number of adsorption steps (FIGS. 1 and 8), illustrating the robustness and the versatility of the method, will allow to tune the biological activity or kinetics of action of the implants by varying the coatings. The present invention is believed to make a significant contribution to the area of regenerative nanomedicine. The concepts found here are applicable to a broad class of tissues and may serve to design sophisticated implants.

Methods for Producing Biomaterials According to the Invention

One aspect of the invention pertains to a method for producing the biomaterial according to the invention described in the above paragraph, said method comprising the steps of:

a) producing or obtaining a nanofibrous scaffold made of biodegradable polymers; and
b) coating said nanofibrous scaffold with at least one layer pair consisting of a layer of polyanions and a layer of polycations, wherein said at least one layer pair incorporates a therapeutic molecule.

Said step of coating the nanofibrous scaffold with at least one layer pair may for example comprise the steps of:
i. immersion of the nanofibrous scaffold in a solution comprising the polycations (e.g. during about 5 to 60 min, preferably during about 15 min);
ii. rinse of the nanofibrous scaffold obtained at the end of step (i) (e.g. during about 5 to 60 min, preferably during about 15 min);
iii. immersion of the nanofibrous scaffold obtained at the end of step (ii) in a solution comprising the polyanions (e.g. during about 5 to 60 min, preferably during about 15 min);
iv. rinse of the nanofibrous scaffold obtained at the end of step (iii) (e.g. during about 5 to 60 min, preferably during about 15 min); and, optionally,
v. repeating step (i) to (iv) for at least a second time; and, optionally,
vi. sterilizing the nanofibrous scaffold obtained at the end of step (iv) or (v) (e.g. by exposure to ultraviolet light).

At step (i) and (iii), the solution comprising the polycations or polyanions may for example comprise a concentration of polycations or polyanions within a range of about 20 to about 500 µM, preferably of about 50 to about 200 µM. Said solution may for example comprise or consist of, in addition to the polyanions or polycations, 0.02 M 2-(N-morpholino)ethanesulfonic acid (MES) and 0.15M NaCl. The pH of the solution is preferably neutral (e.g. a pH of 7.4).

At step (ii) and (iv), the nanofibrous scaffolds may for example be rinsed with a solution having a neutral pH (e.g. a pH of 7.4). Said solution may for example comprise or consist of 0.02 M MES and 0.15M NaCl.

Step (v) may be repeated any number of times, depending on the number of layer pairs that should coat the nanofibrous scaffold. For instance, when building a coating consisting of $(DGL^{G5}\text{-}BMP2)_6$, step (v) consists of five repetitions of steps (i) to (iv).

Step (vi) may for example be carried out by exposure to ultraviolet light (for example at 254 nm, 30 W, at an illumination distance of 20 cm, for about 15 min to about 1 hour, preferably for about 30 min).

Before use, the biomaterial according to the invention may be equilibrated (e.g. by bringing it in contact with serum-free medium).

A detailed protocol that can be used for coating the nanofibrous scaffold is provided in the fourth paragraph of Example 1.

As immediately apparent to the skilled in the art, the steps in which the nanofibrous scaffold is immersed in a solution comprising polycations or polyanions may be replaced with steps wherein said solution is sprayed onto the nanofibrous scaffold.

The above method for producing the biomaterial according to the invention may further comprise the steps of:
c) providing or obtaining living cells (e.g. osteoblatsts or chondrocytes isolated from a patient suffering from a bone and/or cartilage defect);
d) mixing said living cells with a hydrogel (e.g. a collagen hydrogel or an alginate hydrogel); and
e) depositing the mixture obtained at step (d) on the biomaterial obtained at step (b).

Methods for preparing hydrogels are well-known to the skilled in the art. The collagen hydrogel may for example be prepared by mixing collagen (e.g. 3 mL of Rat Tail Type-I Collagen) with a medium containing 10% FBS (e.g. 5.5. mL) and with a 0.1 M NaOH solution (e.g. 0.5. mL). The alginate hydrogel may for example be a mixture of alginate and hyaluronic acid (e.g. an alginate:hyaluronic acid solution (4:1), which may be prepared in a 0.15 M NaCl solution at pH 7.4).

In a specific embodiment, the living cells are osteoblatsts, and the hydrogel is a collagen hydrogel. In the frame of this embodiment, step (d) may be carried out by mixing an osteoblast suspension (e.g. at $2 \times 10^5$ cells·$mL^{-1}$) with the collagen hydrogel (e.g. 1 mL osteoblast suspension mixed with 9 mL of hydrogel). At step (e), the collagen preparation can be poured on the top of the biomaterial obtained at step (b), and may then be incubated in order to allow polymerization (e.g. at 37° C. for about 30 min).

In another specific embodiment, the living cells are chondrocytes, and the hydrogel is an alginate hydrogel. In the frame of this embodiment, step (d) can be performed by mixing a chondrocyte suspension (e.g. at $1 \times 10^5$ cells·$mL^{-1}$) with the alginate hydrogel. At step (e), this preparation can be poured on the top of the biomaterial obtained at step (b).

Before use, cylinders can be cut (e.g. using a sterile biopsy punch), and incubated at about 37° C., e.g. overnight in a humidified atmosphere of 5% $CO_2$.

Alternatively, the living cells may also be directly deposited on the coated nanofibrous scaffold obtained at step (b) or (e), without previous mixture with a hydrogel.

When both osteoblasts and chondrocytes should be deposited on the coated nanofibrous scaffold according to the invention, the above method for producing the biomaterial according to the invention may further comprise, after steps (a) and (b), the steps of:
c) providing or obtaining osteoblatsts (e.g. isolated from a patient suffering from a bone and/or cartilage defect);
d) optionally mixing said osteoblatsts with a collagen hydrogel;
e) depositing the osteoblasts obtained at step (c) or the mixture obtained at step (d) on the biomaterial obtained at step (b);
f) providing or obtaining chondrocytes (e.g. isolated from a patient suffering from a bone and/or cartilage defect);
g) mixing said chondrocytes with a alginate hydrogel; and
h) depositing the mixture obtained at step (g) on the biomaterial obtained at step (e).

These steps (c) to (h) can for example be carried out as described in detail hereabove.

The invention further provides biomaterials obtainable by the methods described herein.

Therapeutic Uses of the Biomaterials According to the Invention

The inventors have shown that the biomaterials according to the invention, functionalized with a growth factor such as BMP2 and optionally with osteoblasts and/or chondrocytes, are very efficient in inducing bone and/or cartilage regeneration (see Examples 3 to 5). In particular, they are suitable for use as implants.

Therefore, the invention pertains to the biomaterial described in the above paragraphs, for use as a bone and/or cartilage defect filling material, or for use in bone and/or cartilage regeneration. The invention also provides the biomaterial described in the above paragraphs, for use in the treatment of a bone and/or cartilage defect. In some embodiments, the biomaterial comprises at least one therapeutic molecule. Preferably, at least one therapeutic molecule is included in the multilayered droplet coat of said biomaterial.

The bone and/or cartilage defect may affect either the bone, or the cartilage, or both. It may for example be a chondral defect, an osteochondral defect, or a subchondral bone defect.

In a specific embodiment according to the invention, the bone and/or cartilage defect is a subchondral bone defect. The invention thus provides a biomaterial described in the above paragraphs for use in subchondral bone regeneration and/or for use in the treatment of a subchondral bone defect.

In particular, the biomaterial according to the invention finds use in the treatment of bone and/or cartilage defect(s) in patients suffering from osteochondritis dissecans, osteonecrosis, osteochondral fracture(s), spinal fusion, a bone and/or cartilage defect due to an injury (e.g. a sport injury or an injury due to an accident), a bone and/or cartilage defect due to ageing, a bone and/or cartilage defect necessitating maxillofacial reconstruction, a bone and/or cartilage defect necessitating sinus lift, a bone and/or cartilage defect necessitating alveolar ridge augmentation, or bone and/or cartilage loss due to a tumor (including benign and cancerous tumors).

In a specific embodiment, the bone and/or cartilage defect is an articular defect, such as e.g. a defect of the knee and/or of the ankle.

In the frame of bone and/or cartilage repair and regeneration, the biomaterial according to the invention may or may not comprise living cells. When it comprises living cells, the cells are preferably autologous cells, i.e. cells isolated from the patient to be treated. As indicated hereabove, these living cells may be comprised within a hydrogel.

When the biomaterial is for use as an implant in the treatment of a small bone and/or cartilage defect (e.g. in the frame of maxillofacial or orthopedic surgery), the biomaterial may be devoid of living cells.

On the other hand, when the bone and/or cartilage defect is a large and/or deep defect, it is preferred that the biomaterial comprises living cells. For instance, when the biomaterial is for use as an implant in the treatment of a large and/or deep bone defect, the biomaterial preferably comprises osteoblasts. When the biomaterial is for use as an implant in the treatment of a large and/or deep cartilage defect, the biomaterial preferably comprises chondrocytes. When the biomaterial is for use as an implant in the treatment of large and/or deep defects affecting the bone and the cartilage (e.g. an osteochondral defect or a subchondral bone defect), the biomaterial preferably comprises both osteoblatsts and chondrocytes.

In a preferred embodiment according to the invention, the biomaterial according to the invention comprises or consists of:
the nanofibrous scaffold made of polymers that is coated with at least one layer pair consisting of a layer of polyanions and a layer of polycations; and
osteoblasts that are optionally comprised within a collagen hydrogel (deposited on said coated nanofibrous scaffold);
and is for use in bone regeneration, and/or in the treatment of a bone defect (preferably a deep and/or large bone defect). Indeed, such a biomaterial is particularly well-suited for the treatment of defects only affecting the bone but not the cartilage.

In another preferred embodiment according to the invention, the biomaterial according to the invention comprises or consists of:

the nanofibrous scaffold made of polymers that is coated with at least one layer pair consisting of a layer of polyanions and a layer of polycations;
osteoblasts that are optionally comprised within a collagen hydrogel (deposited on said coated nanofibrous scaffold); and
chondrocytes that are comprised within an alginate hydrogel (deposited on said coated nanofibrous scaffold);
and is for use in subchondral bone regeneration, in osteochondral regeneration, and/or in the treatment of a subchondral bone defect or an osteochondral defect. In other terms, such a biomaterial is particularly well-suited for the treatment of defects affecting both the bone and the cartilage.

In still another preferred embodiment according to the invention, the biomaterial according to the invention comprises or consists of:
the nanofibrous scaffold made of polymers that is coated with at least one layer pair consisting of a layer of polyanions and a layer of polycations; and
chondrocytes that are comprised within an alginate hydrogel (deposited on said coated nanofibrous scaffold);
and is for use in cartilage regeneration, and/or in the treatment of a cartilage defect.

The invention further provides a method for treating a bone and/or cartilage defect, comprising the step of implanting the biomaterial according to the invention in an individual in need thereof.

In the frame of the present invention, the individual and/or patient to be treated preferably is a human individual and/or patient. However, the biomaterials according to the invention also find use in the field of veterinary medicine.

All references cited herein, including journal articles or abstracts, published patent applications, issued patents or any other references, are entirely incorporated by reference herein, including all data, tables, figures and text presented in the cited references.

Although having distinct meanings, the terms "comprising", "having", "containing' and "consisting of" may be replaced with one another throughout the above description of the invention.

In the frame of the present description, all molecules and cells may optionally be isolated and/or purified.

The invention will be further evaluated in view of the following examples and figures.

Figure 1:
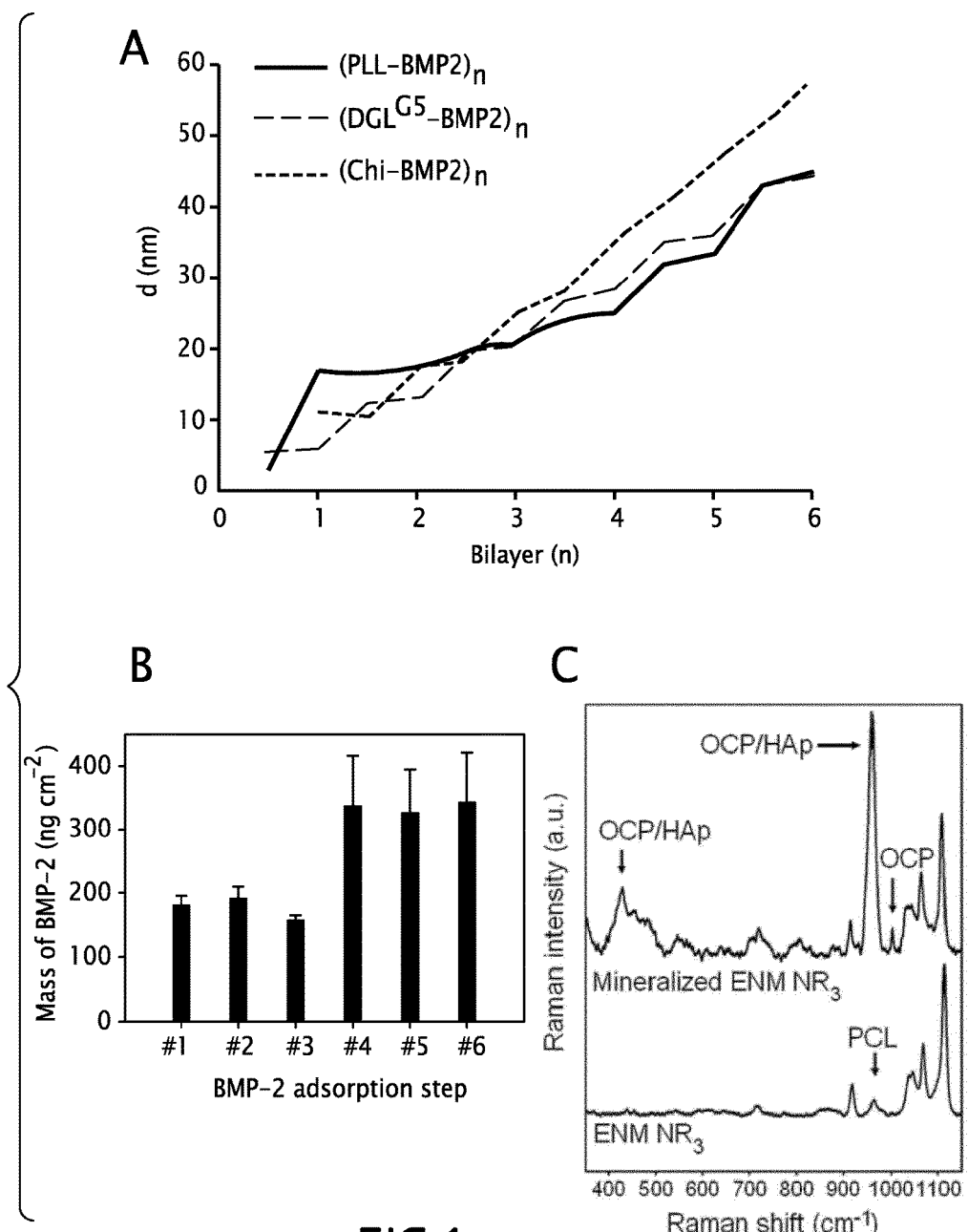
FIG. 1: (A) Quartz Micro Balance (QCM-D) analysis of the incorporation of BMP2 into the multilayers by using:
Dendrigraft poly-Lysine $DGL^{G5}$. 1: $(DGL^{G5}\text{-}BMP2)_1$; 2: $(DGL^{G5}\text{-}BMP2)_2$; 3: $(DGL^{G5}\text{-}BMP2)_3$; 4: $(DGL^{G5}\text{-}BMP2)_4$; 5: $(DGL^{G5}\text{-}BMP2)_5$; 6: $(DGL^{G5}\text{-}BMP2)_6$;
(Poly)lysine polypeptides. 1: $(PLL\text{-}BMP2)_1$; 2: $(PLL\text{-}BMP2)_2$; 3: $(PLL\text{-}BMP2)_3$; 4: $(PLL\text{-}BMP2)_4$; 5: $(PLL\text{-}BMP2)_5$; 6: $(PLL\text{-}BMP2)_6$; and
Chitosan. 1: $(Chi\text{-}BMP2)_1$; 2: $(Chi\text{-}BMP2)_2$; 3: $(Chi\text{-}BMP2)_3$; 4: $(Chi\text{-}BMP2)_4$; 5: $(Chi\text{-}BMP2)_5$; 6: $(Chi\text{-}BMP2)_6$.
(B) Mean wet mass increments upon successive BMP-2 deposition steps derived from the data shown in panel A for $DGL^{G5}$-BMP2 multilayer
(C) Typical Raman spectra of (down) a native and (up) a mineralized $(DGL^{G5}\text{-}BMP2)_3$ membrane (referenced as ENM NR3) (HAp, hydroxyapatite; OCP, octacalcium phosphate). Mineralization was performed by 21-day incubation of the membrane with human osteoblasts in adequate medium. The spectra are offset for sake of clarity.

(B) A front view and a section view of schematic representations of a multilayered droplet coated nanofiber. (C) A front view and a section view of schematic representations a film coated nanofiber.

EXAMPLES

Example 1

Material and Methods

Chemicals

Poly(ε-caprolactone) (PCL), analytical grade, was purchased from Sigma Aldrich. PCL was dissolved in a mixture of dichloromethane/dimethylformamide (DCM/DMF 50/50 vol/vol) at 15% wt/vol and was stirred overnight before use. The Dendri Graft Poly-L-Lysines (DGLs) were purchased from COLCOM (Montpellier, France). In this study, the fifth-generation $DGL^{G5}$ has been used. Human recombinant BMP2 was purchased from PeproTech. Sodium alginate medium viscosity was from Sigma and hyaluronic acid (M.W. 132300) from Lifecore. Rat-tail type I collagen was purchased from Institut de Biotechnologies Jacques Boy. Poly(L-lysine) (PLL) was purchased from Sigma and chitosan (CHI), Protasan up CL 113, was from FMC Biopolymer (Norway). Human recombinant BMP-2 was purchased from PeproTech.

Quartz Cristal Microbalance with Dissipation Monitoring (QCM-D).

QCM-D was operated with a D300 system (Q-Sense, Sweden) using a QAFC302 flow chamber and QSX301 gold-coated quartz crystal sensors. This technique consists of measuring the resonance frequency shifts $\Delta f$ and the dissipation factor changes $\Delta D$ of the quartz crystal sensor upon material deposition (M. V. Voinova, et al. Phys. Scr. 59 (1999) 391-396). The Layer-by-Layer (LbL) buildup was performed by successive injections of polyelectrolyte or protein solutions (5 mL) and rinsing solution (5 mL) through the flow chamber, and monitored in situ. Changes in the resonance frequencies were measured at the third overtone (ν=3) corresponding to the 15-MHz resonance frequency. A shift in $\Delta f$ can be associated, in a first approximation, to a variation of the mass adsorbed onto the crystal through the Sauerbrey relation (G. Sauerbrey, et al, Z. Phys. 155 (1959) 206-222): $m=-C\times\Delta f/v$, where C is a constant characteristic of the crystal used (C=17.7 ng cm-2 Hz-1). CHI (500 µg mL-1) and BMP-2 (200 ng mL-1) were adsorbed by using 0.02 M MES (pH 7.4) and 0.15 M NaCl solutions. Mean thicknesses of the equivalent uniform film were derived from mass values assuming a film density of 1.1 g cm-3 [31].

Electrospinning

A homemade standard electrospinning set-up was used to fabricate the PCL scaffolds. The PCL solution was poured into a 5 mL syringe and ejected through a needle with a diameter of 0.5 mm at a flow rate of 1.2 ml/h, thanks to a programmable pump (Harvard Apparatus). A high-voltage power supply (SPELLMAN, SL30P10) was used to set 15 kV at the needle. Aluminum foils (20×20 cm2), connected to the ground at a distance from the needle of 17 cm, were used to collect the electrospun PCL scaffold.

SEM Observation

For morphological study, the PCL scaffolds were gold-coated (Edwards Sputter Coater) and observed with a Philips XL-30 ESEM scanning electron microscope in conventional mode (high vacuum) with a Thornley-Everhart secondary electron detector.

Polyelectrolyte Multilayers Preparation

For all biological activity experiments, polyelectrolyte multilayers were prepared on Electrospun PCL membrane. Multilayers constituted by $(DGL^{G5}\text{-BMP2})n$ or (PLL-BMP2)n or (CHI-BMP2)n were built by alternating immersion of the surfaces during 15 min in the respective solutions (300 µl) at the respective concentrations of 50 µM for $DGL^{G5}$ or PLL or CHI and 200 nM of BMP2 in presence of 0.02 M MES and 0.15M NaCl at pH=7.4. After each deposition step the membranes were rinsed during 15 min with 0.02 M MES and 0.15M NaCl at pH=7.4. All the membranes were sterilized for 30 min by exposure to ultraviolet (UV) light (254 nm, 30 W, illumination distance 20 cm). Before use, all membranes were equilibrated in contact with 1 ml of serum-free medium (see Cell culture).

In addition, polyelectrolyte multilayers on a Bio-Gide® resorbable collagen membrane (Geistlich Pharma AG, Germany), instead of an Electrospun PCL membrane, were also built.

Cells Culture

Human primary osteoblasts (HOB) were obtain from Cell Applications and cultured in Dulbecco's modified Eagle's medium (D-MEM®) containing 50 U/mL penicillin, 50 µg/mL streptomycin, 2.5 µg/mL Amphotericin B and 10% FBS (Life Technologies, Paisley, UK). The cultures were incubated at 37° C. in a humidified atmosphere of 5% CO2. When the cells reached sub-confluence, they were harvested with trypsin and sub-cultured.

Confocal Raman Microspectroscopy.

Two 5 mm diameter PCL ENM membranes were coated with (DGL, PLL or CHI/BMP-2)n LbL nanoarchitectures. One membrane was stored in the buildup medium, while the other was seeded with human osteoblasts and incubated for 21 days in mineralization medium, then fixed with 4% PFA for 2 hours, rinsed with PBS and finally stored in water. Same mineralization treatment was applied to a native membrane as a reference. The membranes were laid upon a glass substrate and dried under a gentle flow of argon prior to analysis by confocal Raman microspectroscopy. Raman measurements were carried out in air by using a confocal Raman microspectrometer composed of a Raman spectrometer (LabRam HR by Jobin-Yvon Horiba with a 600 lines mm-1 grating) coupled to a microscope (Model BX41, Olympus) with xyz mapping stage via optical fibers (K. C. Schuster, E. et al., J. Microbiol. Meth. 42 (2000) 29-38]. The excitation of Raman scattering was operated with a helium-neon laser at a wavelength of 632.8 nm. The laser beam was focused on the sample by means of a ×50LWD microscope objective. A confocal pinhole of 400 µm diameter placed before the entrance slit was used to reject Raman signal from out-of-focus planes. Raman spectra with good signal-to-noise ratio were recorded with an integration time of 60 s for single spectra and 15 s for 2-D mappings.

Implant Type 2 and Type 3 Preparation $5\times10^4$ human osteoblasts were seeded and incubated for 72 h prior to gel preparation. For the collagen lattices preparation, 3 ml of Rat Tail Type-I Collagen (Institut de Biotechnologies Jacques Boy) were mixed with 5.5 ml of medium containing 10% FBS, 0.5 mL of a 0.1 M NaOH solution and 1 ml of cell suspension at 2×105 cells/ml. 0.5 mL of the cells suspension: collagen preparation were poured on the top of the electrospinned membrane and allow to polymerize by incubating it at 37° C. for 30 min. After polymerization, 0.5 ml of a human chondrocyte suspension (1×105 cells/ml) in an alginate hyaluronic acid solution (4:1) prepared in 0.15 M NaCl, pH 7.4 were poured on the top of the collagen lattice in order to obtain the 3-layered construct. 5 mm or 2 mm cylinders were cute using an sterile biopsy punch and incubated o/n at 37° C. in a humidified atmosphere of 5% $CO_2$ prior to in vivo experiments Cell Viability and Proliferation Cell viability was determined by trypan blue exclusion. AlamarBlue® (Serotec) was used to assess cellular proliferation. The Alamar Blue test is a non-toxic, water-soluble, colorimetric redox indicator that changes color in response to cell metabolism. In this study, $2 \times 10^4$ human osteoblasts were seeded on the top of LbL-coated 14 mm-diameter membranes (n=3) placed on 24-well plates. After 2 days of culture, cells were incubated in 10% AlamarBlue/DMEM solution in a humidified atmosphere at 37° C. and 5% CO2. After 4 hours, 100 mL of incubation media was transferred to 96-well plates and measured at 590 nm and 630 nm in order to determine the percentage of AlamarBlue reduction.

Immunofluorescence

Cells were fixed with 4% PFA during 1 hour, permeabilized with 0.1% Triton X-100 for 1 hour and incubated for 20 min with Alexa Fluor 546-conjugated phalloidin (Molecular Probes) for F-actin labeling and 5 min with 200 nM DAPI (Sigma) for nuclear staining. Cells were mounted on microscope slides using Vectashield (Vector) and imaged by confocal microscopy (Zeiss, LSM 510).

Confocal Laser Scanning Microscopy (CLSM)

CLSM observations were documented with a Zeiss LSM 510 microscope using a ×40/1.4 oil immersion objective at 0.4 μm z-section intervals. FITC fluorescence was detected after excitation at 488 nm with a cutoff dichroic mirror 488 nm and an emission band-pass filter 505-530 nm (green).

Statistical Analysis

All values are expressed as mean±SEM and all experiments were repeated at least three times. Statistical analysis was performed using the Mann Whitney U test. A probability p value <0.05 was considered significant to reject the null hypothesis.

Example 2

Scaffolds for Use in Bone and/or Cartilage Regeneration

Until now, different studies have focused on either bone or cartilage regeneration and never on the restoration of the entire osteo-chondral unit. The present invention proposes a new strategy based on ECM synthetic materials to restore the osteochondral unit.

In order to create scaffolds or ECM analogues, which are truly biomimicking at the ECM scale (proteins range in diameter from 50 to 500 nm), one must employ nanotechnology. Recent advances in nanotechnology have led to a variety of approaches for the development of engineered ECM analogues. To date, three processing techniques (self-assembly, phase separation, and electrospinning) have evolved to allow the fabrication of nanofibrous scaffolds. With these advances, the long-awaited and much anticipated construction of a truly "biomimicking" or "ideal" tissue engineered environment, or scaffold, for a variety of tissues is now highly feasible.

The intricate fibrillar architecture of natural ECM components has inspired several researchers to produce materials with similar structure. Upon fibers that are tens of microns in diameter, cells seem to respond as though to a 2-D substrate, acquiring an unnatural flat shape, leading to a nonphysiological, asymmetrical occupation of adhesion receptors; notwithstanding, such matrices have already shown remarkable success in tissue engineering applications, such as in the reconstruction of a dog urinary bladder (Oberpenning et al. 1999 Nat Biotechnol 17:149-155) or as scaffolds for neural stem cells to facilitate regeneration after brain injury in a mouse stroke model (Park et al. 2002 Nat Biotechnol 20:1111-1117). Polymer processing technologies such as electrospinning (Kenawy et al. Biomaterials 2003 24:907-913) allow fiber formation down to the 10 nm scale.

In this study, the PCL polymer (Poly(ε-caprolactone)) has been used to create a membrane composed of electrospun nanofibers as a scaffold. PCL is degraded by hydrolysis of its ester linkages under physiological conditions (such as in the human body) and has therefore received a great deal of attention for use as an implantable biomaterial. In particular it is especially interesting for the preparation of long-term implantable devices, owing to its degradation, which is even slower than that of polylactide. PCL is an Food and Drug Administration (FDA) approved material that is used in the human body as, for example, a drug delivery device, suture (sold under the brand name Monocryl or generically), or adhesion barrier.

For tissue engineering applications, it is generally recognized that an inert ECM mimetic scaffold is not sufficient to generate a durable repair. There is a need for sophisticated and active materials that incorporate, for example, growth factors that would be released in a sustained manner.

In recent years, considerable effort has been devoted to the design and controlled fabrication of structured matrices with functional properties (Zhang et al. 2003 Nat Biotechnol 21:1171-1178).

Polyelectrolyte multilayer (PEM) films incorporating functional proteins and other bioactive materials provide one example (Lynn. 2006 Soft Matter 2:269-273). PEM films are prepared by the layer-by-layer (LbL) deposition of interacting materials, typically by the electrostatic interaction of oppositely charged polyelectrolytes (Decher. 1997 Science 277:1232-1237). Therapeutics and biomolecules including peptides, proteins, and nucleic acid have been embedded in PEM films, which offer new opportunities for the preparation of functionalized bioactive coatings (Lynn. 2006 Soft Matter 2:269-273; Decher. 1997 Science 277:1232-1237; 15. Jesse) et al. 2003 Advanced Materials 15:692-695). These supramolecular nanoarchitectures can be designed to exhibit specific properties, including control of cell activation, inflammation (Benkirane-Jessel et al. 2004 Advanced Materials 16:1507; Benkirane-Jessel et al. 2004 Adv Funct Mater 14:174-182) and localized drug, growth factor or nucleic acid delivery (Jesse) al. 2006 Proc Natl Acad Sci USA 103:8618-8621; Kim et al. 2008 ACS Nano 2, 386-392). The embedded biomolecules, which are either chemically bound to polyelectrolytes or physically adsorbed, have been shown to retain their biological activity in many studies (Benkirane-Jessel et al. 2004 Advanced Materials 16:1507; Benkirane-Jessel et al. 2004 Adv Funct Mater 14:174-182; Jesse) al. 2006 Proc Natl Acad Sci USA 103:8618-8621; Kim et al. 2008 ACS Nano 2, 386-392; Benkirane-Jessel et al. 2005 Adv Funct Mater 15:648-654). Bioactive proteins can be directly integrated in the architecture without any covalent bonding with a polyelectrolyte and keep a secondary structure close to their native form. Degradable-layered structures appear, therefore, to be highly advantageous for progressive delivery of associated active agents (Dierich et al. 2007 Advanced Materials 19:693-697; Facca et al. 2010 Proc Natl Acad Sci USA 107:3406-3411; Krogman et al. 2009 Nat Mater 8:512-518; Barnes et al. 2007 Adv Drug Deliv Rev 59:1413-1433; Yoo et al. 2009 Advanced Drug Delivery Reviews 61:1033-1042; Fioretti et al. 2010 ACS Nano 22:3277-3287).

The inventors provide a novel strategy for generating subchondral bone couples the use of an active matrix, with cellularized hydrogels.

In this study, BMP2 has been used as a growth factor to functionalize electrospun nanofibers (ENM) of PCL (Poly (ε-caprolactone)).

Example 3

Building and Study of Implant Type 1

Recently, the inventors have reported that by using PLL (Poly-L Lysine) or a Dendri-Graft of Lysine (DGL) to incorporate an active peptide into a multilayered film, it is possible not only to modulate inflammation but also to increase the proliferation of cells in contact with this multilayered film (Fioretti et al. 2010 ACS Nano 22:3277-3287).

In this study, the inventors have chosen to use DGL and the active growth factor BMP2 that stimulates bone induction (BMP2 is already clinically approved for bone regeneration). To analyze the incorporation of BMP2 into the multilayered films (DGL/BMP2), the build up was followed by (Quartz micro balance, QCM-D) and a linear increase of thickness was shown after each deposition (FIG. 1).

Figure 3:
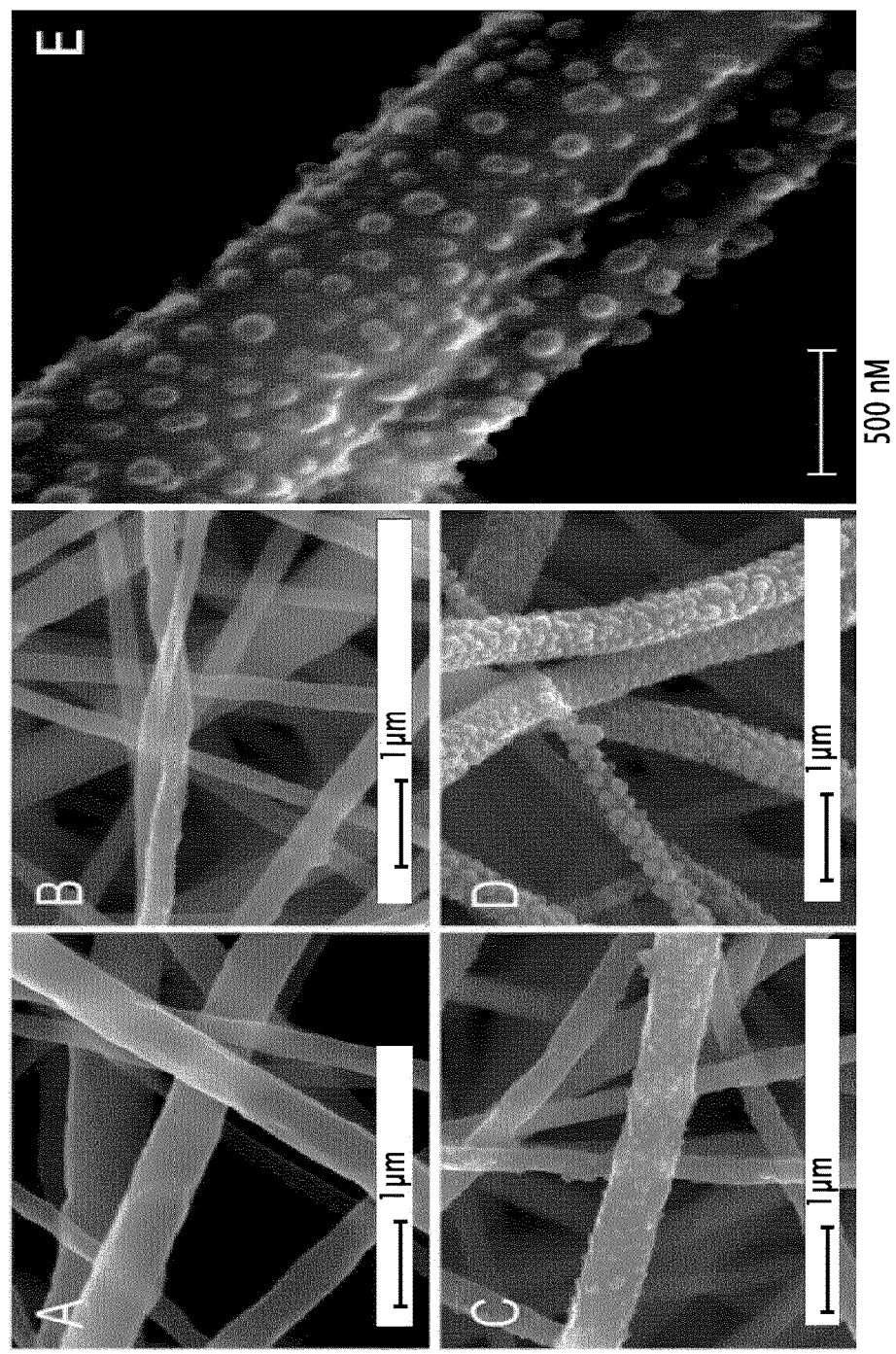
FIG. 3: SEM visualization of the electrospun Poly(ε-caprolactone) nanofibers during the build up and the incorporation of BMP2 into the multilayered electrospun membranes $(DGL^{G5}\text{-}BMP2)_n$. (A) Electrospun membrane (B) $(DGL^{G5}\text{-}BMP2)_1$ (C) $(DGL^{G5}\text{-}BMP2)_3$ (D) $(DGL^{G5}\text{-}BMP2)_6$ (E) detail view of C: $(DGL^{G5}\text{-}BMP2)_3$

FIG. 3 shows SEM images (×20.000) of membranes showing the layer-by-layer deposition of nanoreservoirs (NRn) incorporating BMP-2. Different nano-structures can be observed from one pair of layer deposition (NR1 (FIG. 3B) comparing to the uncoated membrane NR0 (FIG. 3A). The nanoreservoirs are clearly identifiable with 3 (NR3 FIGS. 3C and 3E) or 6 layer pairs (NR6, FIG. 3D).

As observed on FIG. 3E (zoomed SEM image of FIG. 3C (×35.000), scale bars: 1 μm) the coating doesn't cover the totality of the nanofibers surface. The coating is constituted by the deposition of polymers patches, layer-by-layer on small surfaces of the nanofiber until the constitution of multilayered droplet (FIGS. 3B, C, D and E). Few droplets are observed with 1 pair of layer deposition (FIG. 3 B), the number of droplets grows with numbers of pair layer depositions. According to the invention, the deposition is stopped before getting a film coating.

Mean wet mass increments upon successive BMP-2 deposition steps derived from the data shown in FIG. 1A. Each BMP-2 injection step resulted in the immobilization of about 180 ng cm$^{-2}$ BMP-2 up to the NR3 architecture, and about 330 ng cm$^{-2}$ for further steps (FIG. 1B). This difference is not unexpected considering that a few adsorption steps are generally required to overcome the possible influence of the underlying substrate and, in turn, to reach a steady layer-by-layer growth regime.

To analyze more deeply the capacity of these membranes to induce bone mineralization, an ENM NR3 membrane was inspected by confocal Raman microspectroscopy after 21-day in vitro mineralization by human osteoblasts, to detect calcium phosphate (CaP) deposition. A nonmineralized ENM NR3 membrane was analyzed as a reference. Raman signatures are very similar (FIG. 10), except in the region around 960 cm$^{-1}$ relative to CaP, where the signatures of the mineralized membrane show a significant peak proving the presence of CaP, contrary to the unmineralized membrane. Raman signatures of the latter display a weak peak at 963 cm$^{-1}$ relative to PCL, whose contribution to the CaP peak on mineralized membranes is negligible. A 2-D mapping of the CaP peak intensity over the mineralized membrane (data not shown), reveals a massive CaP deposition all over the ENM NR3 membrane. The peaks at 960 cm$^{-1}$ and 430 cm$^{-1}$ (FIG. 10) reveal the presence of hydroxyapatite (HAp) and/or octacalcium phosphate (OCP), while the peak at 1005 cm$^{-1}$ is unambiguously attributable to OCP. If the coating was pure OCP, a shoulder should be present at 966-970 cm$^{-1}$. The absence of such a feature is necessarily due to the overwhelming contribution of the HAp peak, which indirectly confirms the coexistence of HAp and OCP. The presence of OCP is not surprising as it is a precursor phase of HAp in bone.

Figure 2:
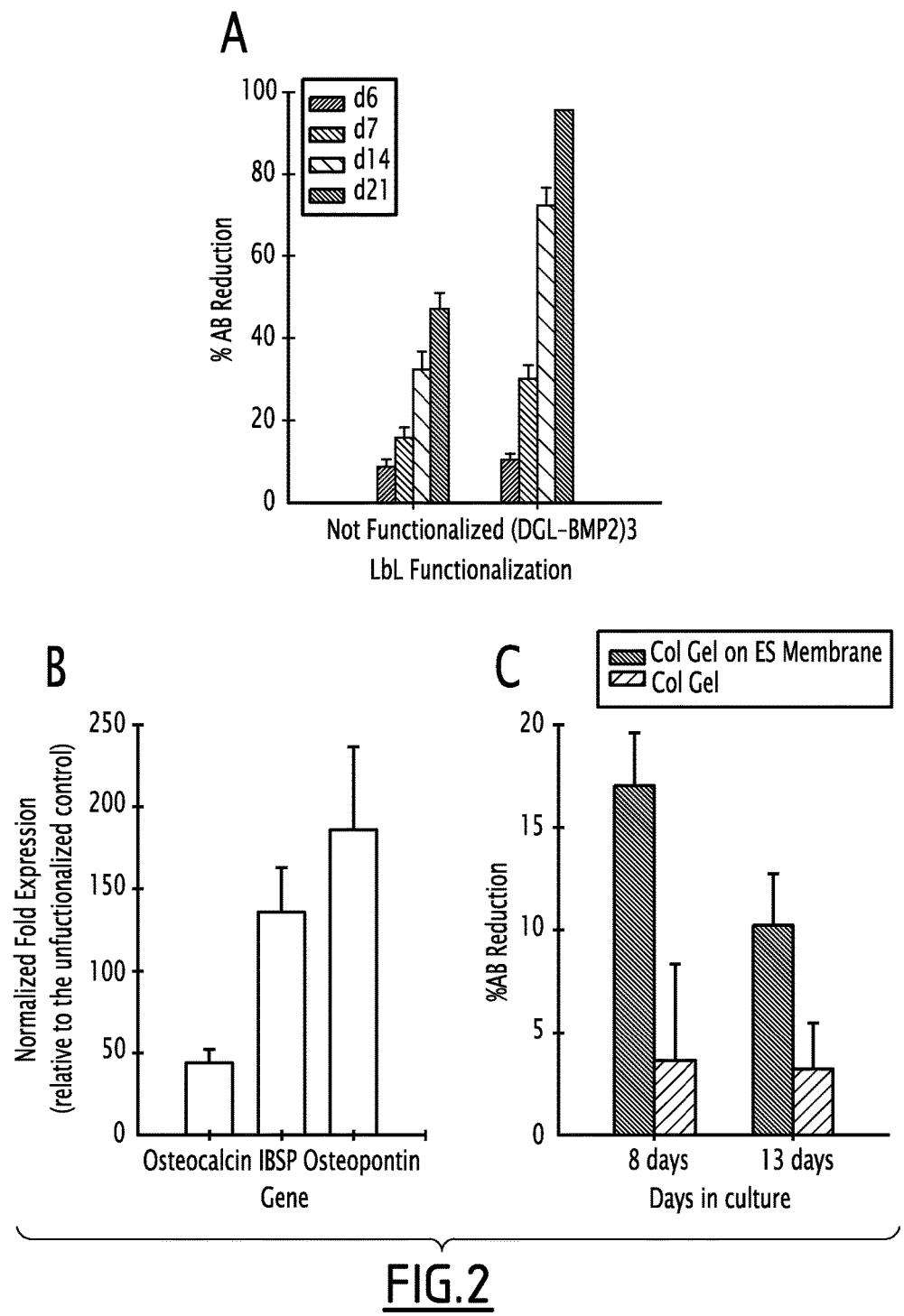
FIG. 2: (A) In vitro proliferation of human osteoblasts growing on the surface of the multilayered electrospun nanofibers membranes: $(DGL^{G5}\text{-}BMP2)_3$. "% AB Reduction" stands for the percentage of AlamarBlue reduction. (B) Differences in gene expression monitored by qPCR of osteoblastic markers in human osteoblasts cultured on $(DGL^{G5}\text{-}BMP2)_3$ functionalized electrospun membranes as compared with not-functionalized matrices. (C) Proliferation of osteoblasts 3D-cultivated in lattices of type I collagen deposited on the electrospun membranes.

The capacity of these multilayered films, in the presence of human osteoblasts, to induce specific gene expression has also been analyzed by immunochemistry. By using this multilayered film as a coating for an electrospun nanofiber membrane (ENM), an increase in the proliferation of human osteoblasts was observed in vitro (FIG. 2A), and also an increase in the expression of specific genes when these cells were cultured on (DGL$^{G5}$-BMP2)$_3$ functionalized membranes for 7 days; respectively, 43.7 (±8.8) osteocalcin gene expression, 135.3 (±27.5) integrin-binding sialoprotein (IBSP) gene expression, the major structural protein of the bone matrix, and 186.2 (±50.1) osteopontin gene expression, fold higher compared to cells grown on non-functionalized membranes (FIG. 2B).

The efficiency of this nanostructured BMP2 active ENM to induce bone formation in vivo after 30 days of implantation was analyzed by the expression of osteopontin (data obtained by immunofluorescence, not shown).

At this step, the results indicate clearly that using the present invention, it is possible to:

(i) design an ENM implant (thickness and size controlled), incorporating BMP2 reservoirs (Implant Type 1, see Table 1 herebelow); and (ii) induce bone formation in vitro and in vivo.

This membrane could be used for small lesions of bone without any need to add cells from patients. Unfortunately, for large and deep lesions it becomes necessary to add osteoblasts from the patient. In the clinic today, surgeons use collagen membranes (animal origin) that slowly induce bone formation, and that cannot be used for all types of lesion.

Example 4

Building and Study of Implant Type 2

In this study, a cellularized collagen matrix (human osteoblasts, GMP clinical grade) was deposited on the membrane (Implant Type 1, i.e. an implant obtained as described in example 3 hereabove) to fabricate a nanostructured active living membrane (Implant Type 2, see Table 1 herebelow). It was shown that such an implant can induce bone induction.

It was also shown that by using stem cells (embryonic stem cells) growing on the surface of the active membrane (reservoirs of BMP2), it was possible to induce bone regeneration (data obtained by immunofluorescence, not shown).

In FIG. 2C, increased human osteoblast proliferation was observed by using a collagen matrix including cells, built on an ENM including the active reservoirs of BMP2, than by using collagen matrix without membrane support).

As previously mentioned, in the absence of an intact subchondral bed (bone), treatment of a surface chondral lesion is prone to failure. The present invention reports the first demonstration of an active living nanostructured hybrid membrane for subchondral bone regeneration. These promising results point to potentially far more efficient surgical approaches than are currently available.

The building of Implant Type 1, Type 2 and Type 3 is summarized in Table 1 herebelow.

TABLE 1

Step by step fabrication of nanostructured active and living
membranes for bone osteochondral bone regeneration STEP 1  (A) PCL membrane electrospinning process yielding electrospun nanofibers
(B) Functionalization of the PCL membrane (build up of the nano-reservoirs
by an alternate adsorption of polycation (the polyelectrolyte preferably being a
polypeptide or a polysaccharide) and oppositively charged therapeutic
molecules (protein, peptides, chemical molecule, DNA, siRNA, etc.)
(C) Membrane punched out at size required for in vitro experiment (14 mm, or
any needed size)
Generation of a novel, stable and easy-to-handle implant for rapid bone
regeneration in small lesions ("Implant Type 1", or "Active Membrane")

Figure 4:
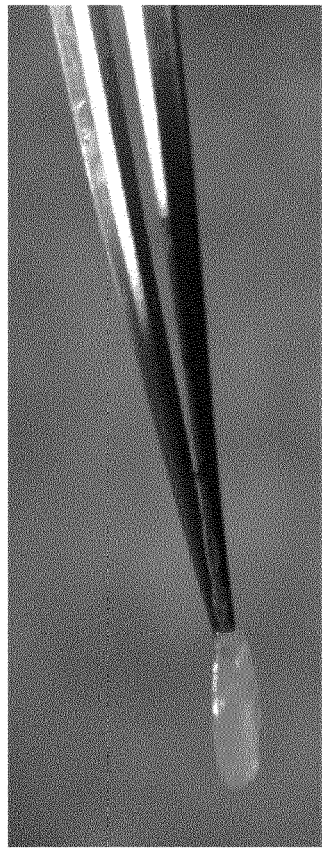
FIG. 4: The left picture shows an implant Type 2 that is an electrospun PCL membrane functionalized by active nano-reservoirs of BMP2 and mixed collagen/human osteoblasts from patients. This implant generates a novel, stable and easy-to-handle implant for rapid bone regeneration in large lesions (Implant Type 2—Active Living Membrane). This composite matrix represents a promising approach for the rapid regeneration of bone in large lesions. The right picture shows an implant Type 3. This implant corresponds to the implant type 2 coated with mixed Human chondrocytes/alginate+hyaluronic acid. The resulting hybrid active nanostructured living biomaterial represents a unique type of implant offering the possibility of reliable, rapid, "seamless", and therefore very durable, regeneration of osteochondral lesions (Implant Type 3—Active Hybrid Living Membrane).
Figure 4:
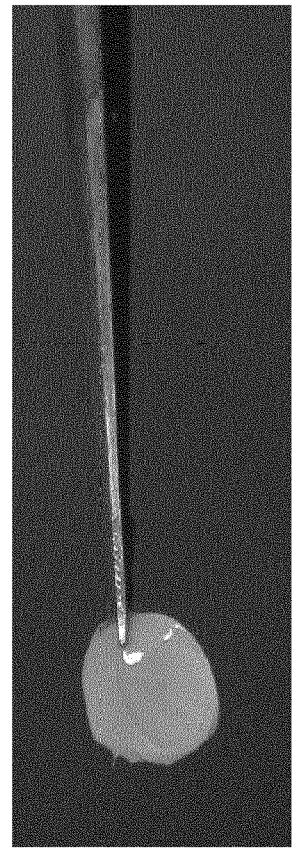

STEP 2  Human osteoblasts, optionally mixed with collagen, are deposited on the
active membrane from Step 1.
Generation of a complex matrix ("Implant Type 2"), which represents a
promising approach for the rapid regeneration of bone in large lesions (see
e.g. FIG. 4, left picture).

STEP 3  Human chondrocytes are mixed with alginate and hyaluronic acid, and
deposited as a gel or spayed on the membrane from step 2.
Generation of a hybrid active nanostructured living biomaterial ("Implant
Type 3") that represents a unique type of implant offering the possibility of
reliable, rapid, "seamless", and therefore very durable, regeneration of
osteochondral lesions (see e.g. FIG. 4, right picture).

Example 5

Further Studies with the Scaffolds with Nano-Reservoirs of Therapeutic Molecules In FIG. 3 we report how it is possible to incorporate the growth factor BMP2 as an active nanostructured coating on the electrospun nanofibers. We can see here how this coating can be built layer-by-layer and note the nanostructured organization surrounding the nanofibers as nano-reservoirs.

The efficiency of a type 2 Implant for promoting bone repair was studied in vivo in a mouse model. After 2 months of implantation on nude mice (males, 16 week-old), nano-mechanical analysis of the retrieved implants showed an increased elastic modulus (2.19±0.39 GPa) for the Implant Type 1 NanoM1 device in comparison with the ENM NR0 membrane (1.74±0.65 GPa), which is likely due to the effect of the incorporated BMP-2. Promisingly, the highest value of elastic modulus was measured for an Implant Type 2 membrane enriched with Osteoblasts (14.26±2.16 GPa).

The treatment goal for large chondral or osteochondral defects should be to restore the physiological properties of the entire osteochondral unit, aiming to achieve a more predictable repair tissue that closely resembles the native articular surface and remains durable over time. The inventors report here the first demonstration of subchondral bone regeneration using a strategy based on a synthetic nanoengineered electrospun membrane manufactured using an FDA-approved polymer and functionalized with nanoreservoirs of a growth factor (BMP-2).

Figure 5:
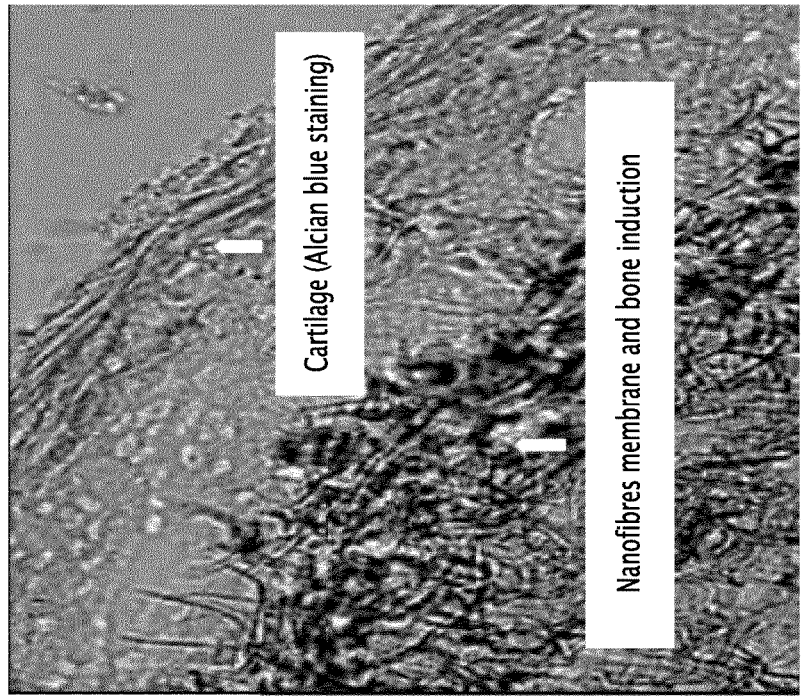
FIG. 5 shows in vivo osteochondral regeneration in a mouse model. The result was obtained using an Active living hybrid implant (i.e. a membrane comprising nano-reservoirs of BMP2, human osteoblatsts, and human chondrocytes in an alginate/hyaluronic acid hydrogel).
Figure 5:
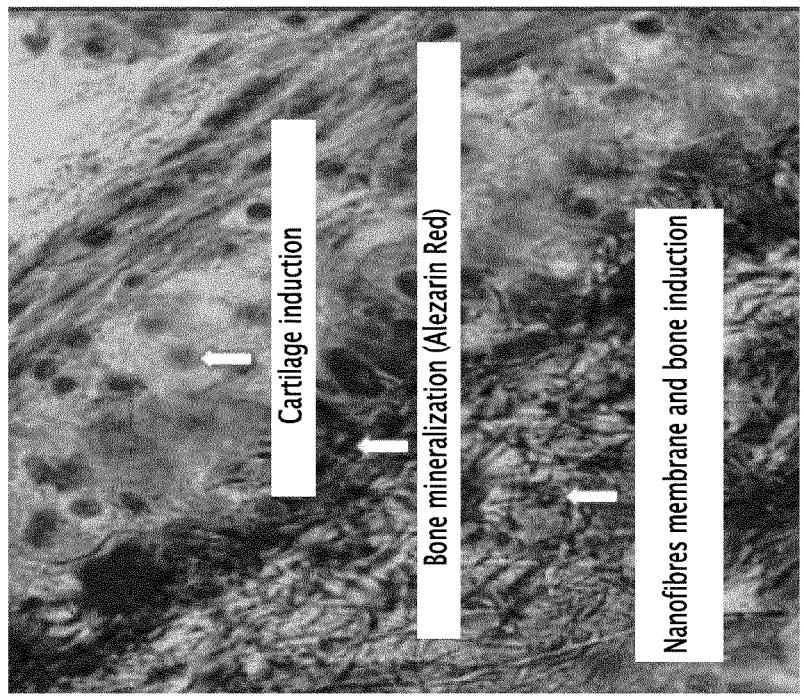

Indeed, the inventors shown that such implants are able to induce bone regeneration (FIG. 5). In particular, the results clearly demonstrate that osteoblast colonization of the nanofiber membrane does occur, and that mineralization also occurs.

Figure 7:
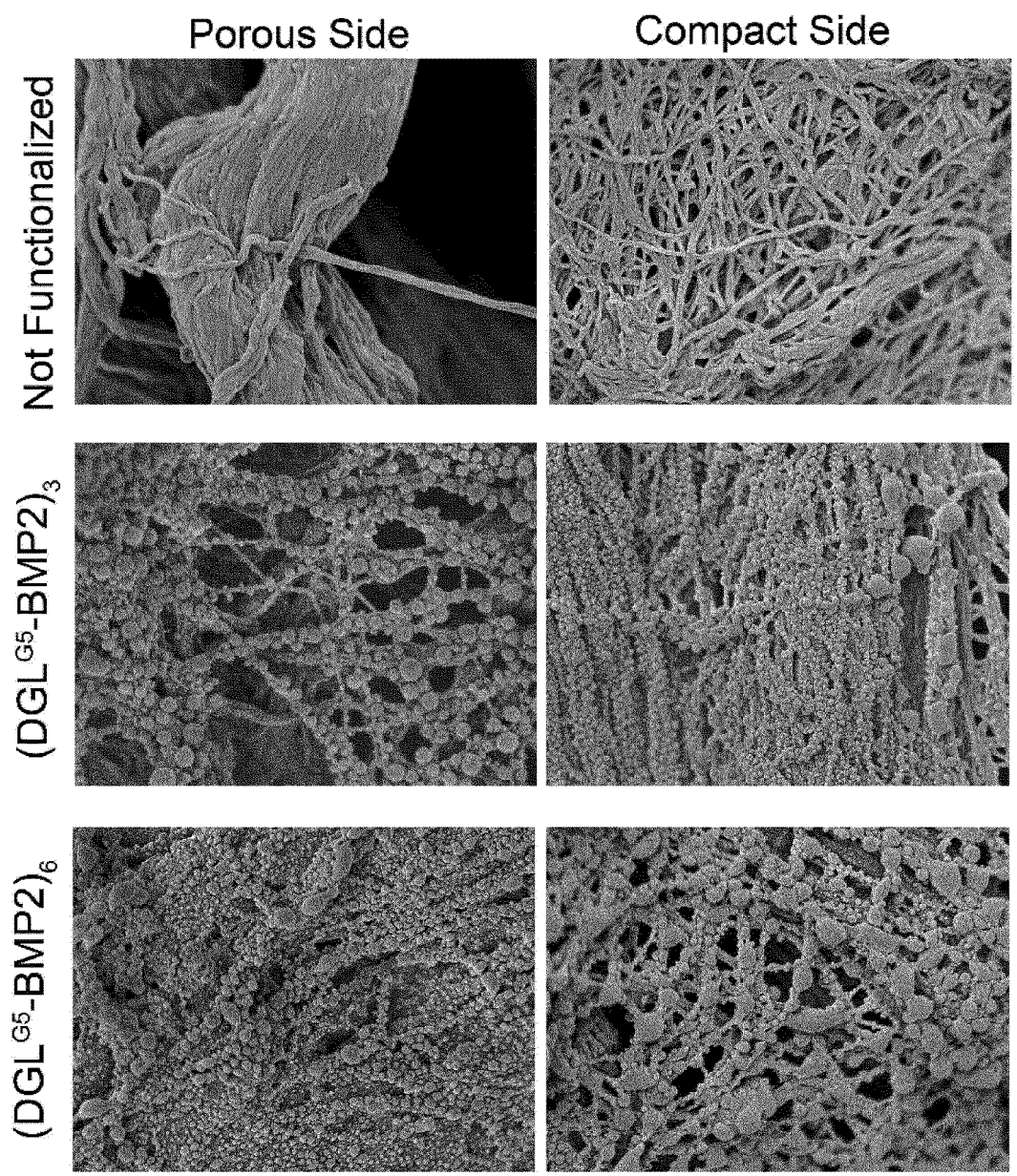
FIG. 7: SEM visualization of a Bio-Gide® resorbable collagen membrane (Geistlich Pharma AG, Germany) before and after coating with $(DGL^{G5}\text{-}BMP2)_3$ or $(DGL^{G5}\text{-}BMP2)_6$. Left column: porous side of the Bio-Gide® resorbable collagen membrane. Right column: compact side of the Bio-Gide® resorbable collagen membrane.

It was shown that an implant of type 1 can also be built using a Bio-Gide® resorbable collagen membrane (Geistlich Pharma AG, Germany) as a nanofibrous scaffold rather than electrospun poly(ε-caprolactone) nanofibers (see FIG. 7).

Figure 6:
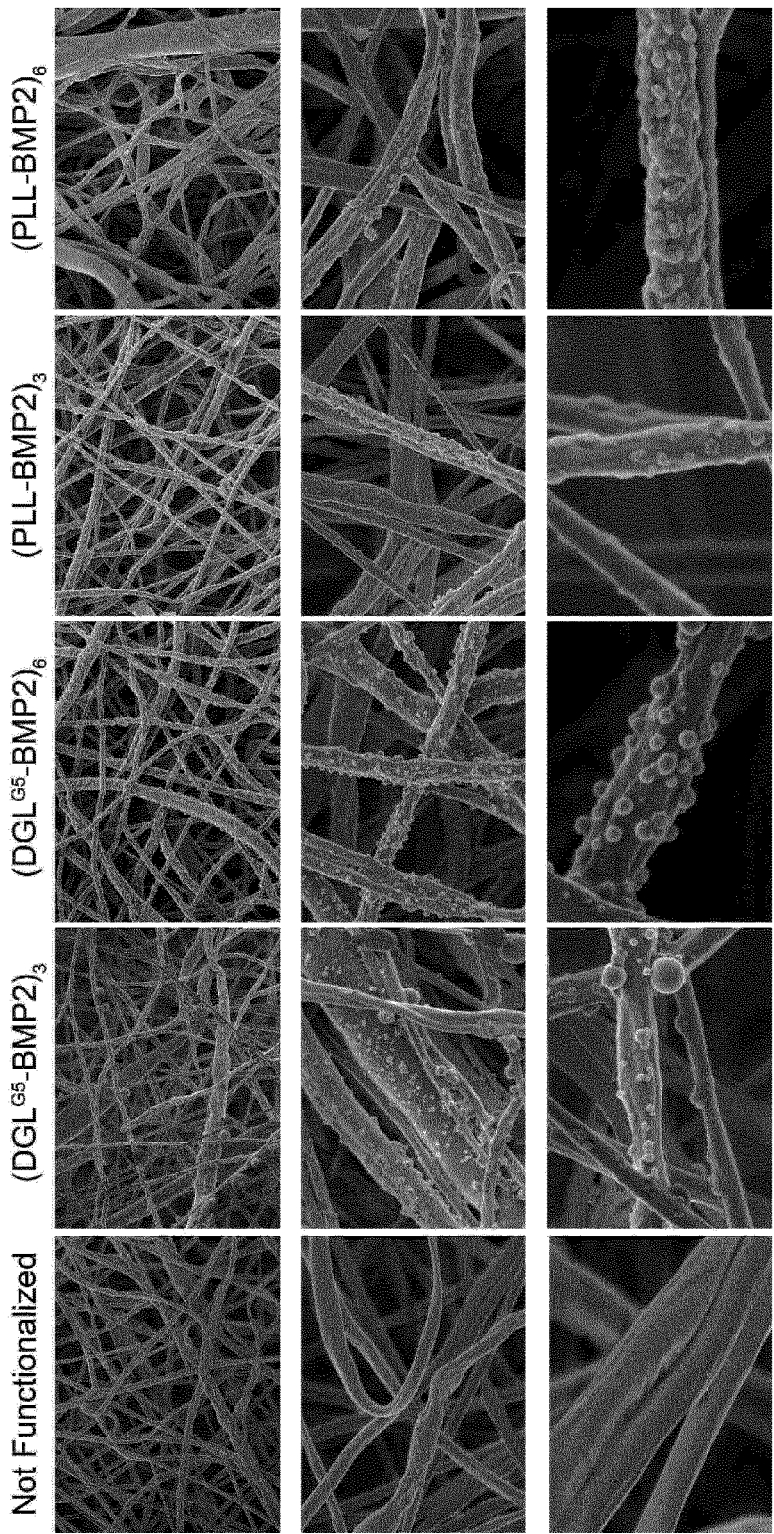
FIG. 6: SEM visualization of an electrospun Poly(ε-caprolactone) nanofibrous scaffold that is either not coated, or coated with $(DGL^{G5}\text{-}BMP2)_3$, $(DGL^{G5}\text{-}BMP2)_6$, $(PLL\text{-}BMP2)_3$ or $(PLL\text{-}BMP2)_6$.

It was further shown that not only $(DGL^{G5}\text{-BMP2})n$, but also (PLL-BMP2)n and (Chitosan-BMP2)n, were suitable for obtaining nano-reservoirs of active molecules (see FIGS. 1 and 6).

Example 6

Electrospun Nanofibrous Membrane of Poly(ε-Caprolactone) (PCL) Polymer Coated with Chitosan and BMP-2

Figure 8:
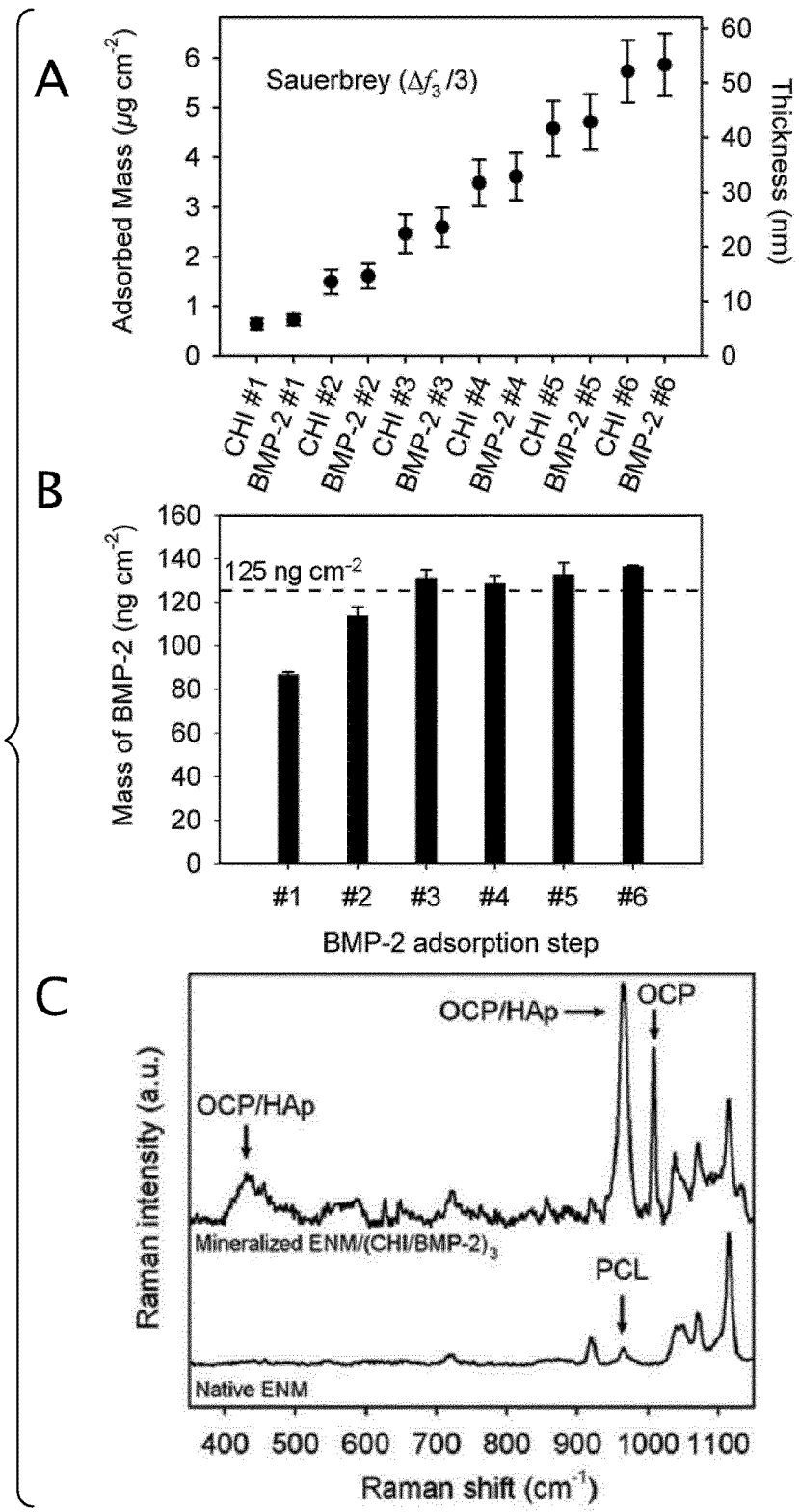
FIG. 8: (A) Mean adsorbed mass and thickness evolutions over 2 distinct experiments during the buildup of $(CHI/BMP\text{-}2)_6$ LbL nanoarchitectures onto gold-coated quartz sensors followed by QCM-D. Thickness values were derived from mass values postulating an equivalent uniform film of 1.1 g cm$^{-3}$ in density. (B) Mean mass increments upon successive BMP-2 deposition steps derived from data in (A). Error bars represent the standard errors. (C) Typical Raman spectra obtained from (down) a non-mineralized native and (up) a mineralized $(CHI/BMP\text{-}2)_3$-treated ENM scaffold (HAp: hydroxyapatite; OCP: octacalcium phosphate). Similar spectra were obtained for mineralized native and $(PLL/BMP\text{-}2)_3$-treated scaffolds. Mineralization was performed by 21-day incubation of the scaffolds with human osteoblasts in adequate medium. Spectra are offset for sake of clarity.

The effective buildup of CHI/BMP-2 LbL architectures onto gold-coated substrates was demonstrated by QCM-D up to 6 adsorption cycles. It followed a linear growth regime, with deposited mass increments of about 1.1 µg cm$^{-2}$ (corresponding to 10 nm in equivalent uniform thickness) upon each new deposited CHI/BMP-2 layer pair (FIG. 8A). The mean amount of growth factor immobilized upon each BMP-2 adsorption step (from step #2 to step #6) was 125±7 ng cm$^{-2}$ (FIG. 8B). It was not unexpected that the adsorbed amount of BMP-2 was slightly lower at steps #1 and step #2 than at later steps considering that a few adsorption steps are generally required to overcome the possible influence of the underlying substrate and, in turn, to reach a steady Layer-by-Layer growth regime (K. Abdelkebir, et al; Soft Matter 7 (2011) 9197-9205).

Figure 9:
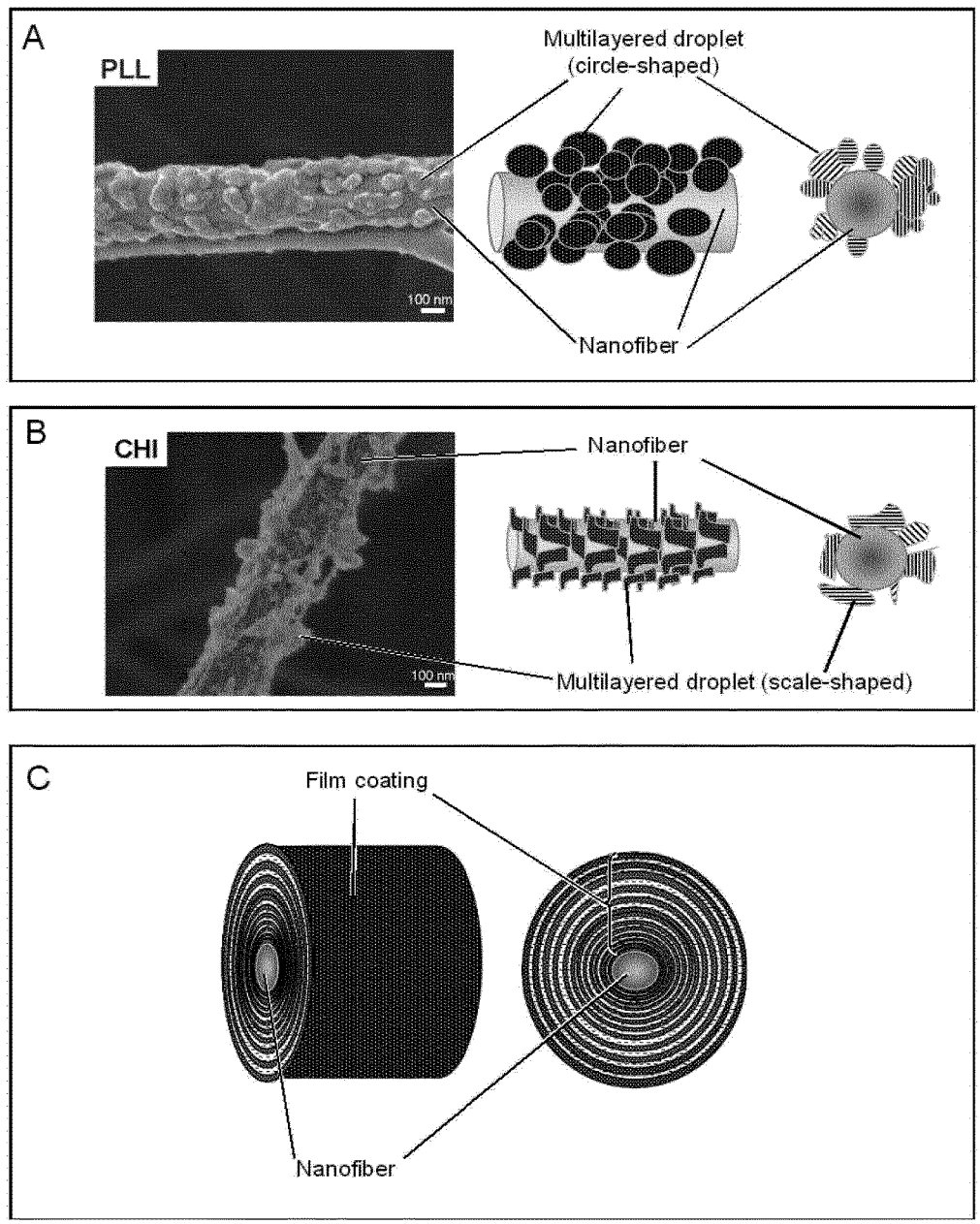
FIG. 9: (A) A front view and a section view of schematic representations of a multilayered droplet coated nanofiber.

The effective deposition, and nanoscale dimensions, of the bioactive LbL architectures onto electrospun nanofibrous membrane (ENM) substrates were confirmed by means of scanning electron microscopy (SEM). The smooth morphology of native nanofibers gave place to uniformly distributed nanostructured deposits around (CHI/BMP-2)$_3$-treated nanofibers (FIG. 9B). Observed changes in the nanofibers roughness could also affect cell behavior along with the chemistry changes induced by the LbL treatment.

With an isoelectric point of 8.0-8.5 (M. Geiger, et al Adv. Drug Deliv. Rev. 55 (2003) 1613-1629; T. Crouzier, et al., Small 5 (2009) 598-608; M. L. Macdonald, et al, Biomaterials 32 (2011) 1446-1453) BMP-2 is an almost neutral protein, with a slightly positive global charge under the physiological conditions (pH 7.4) (S. Chen, et al, Sci. Technol. Adv. Mater. 12 (2011) 065003). This is an amphoteric elongated protein with a positively charged central domain and negatively charged domains at both extremities (C. Scheufler, et al, J. Mol. Biol. 287 (1999) 103-115). CHI has a pKa of 6.5, therefore at pH 7.4 the amount of protonized amine moieties is very low, such that CHI is also weakly positively charged. Considering the repulsive electrostatic interactions between similarly charged CHI and BMP-2, the effective buildup of LbL coatings comprised of these macromolecules may appear, in a first approach, as rather unexpected.

Human osteoblasts (HOB cells) adhesion after 24-h culture was clearly promoted onto (CHI/BMP-2)$_3$-treated ENM scaffolds compared to native scaffolds, resulting in larger, far more spread and elongated cells anchored to nanofibers through numerous filopodia extensions (data not shown). In line with recently published data (K. Anselme, et al, Acta Biomater. 6 (2010) 3824-3846; I. Wheeldon, et al, Nanotechnology 22 (2011) 212001), morphology changes between cells adhering onto native and LbL-treated ENM scaffolds are likely to be due to the combined modifications of both the surface chemistry and nanotopography upon the LbL treatment. The capacity of the modified ENM scaffolds to induce in vitro specific gene expression by HOB cells was verified by immunochemistry (data not shown). Accordingly, the proliferation of HOB in vitro was much enhanced onto treated, compared to untreated, ENM scaffolds (data not shown). The inventors have also analyzed as a negative control the incorporation of an inert protein (albumin, BSA) into the multilayered coating and shown no osteopontin expression by HOB cells (data not shown).

In order to inspect more deeply the capacity of these scaffolds to induce bone mineralization, a (CHI/BMP-2)$_3$-treated ENM scaffold was analyzed by confocal Raman microspectroscopy after 21-day in vitro mineralization by HOB cells, to detect calcium phosphate (CaP) deposition. A scaffold treated using poly(L-lysine) (PLL) instead of CHI was also analyzed in order to test the versatility of the LbL method for embedding BMP-2 onto ENM fibers. A native non-mineralized scaffold was analyzed as a reference. Raman signatures were very similar for all scaffolds, except in the regions around 430 cm$^{-1}$ and 960 cm$^{-1}$ relative to CaP, where signatures of the mineralized scaffolds showed significant peaks proving the presence of CaP, contrary to the non-mineralized scaffold (FIG. 8C). Raman signatures of the latter displayed a weak peak at 963 cm$^{-1}$ relative to PCL, whose contribution to the CaP peak on mineralized membranes was negligible (P. Taddei, et al, J. Mol. Struct. 744-747 (2005) 135-143). The peaks at 430 cm$^{-1}$ and 960 cm$^{-1}$ revealed the presence of hydroxyapatite (HAp) and/or octacalcium phosphate (OCP), while the peak at 1005 cm$^{-1}$ was unambiguously attributable to OCP (B. O. Fowler, et al, Chem. Mater. 5 (1993) 1417-1423; N. J. Crane, et al, Bone 39 (2006) 434-442). For pure OCP coating, a shoulder should be present at 966-970 cm$^{-1}$ (B. O. Fowler, et al, Chem. Mater. 5 (1993) 1417-1423; N. J. Crane, et al, Bone 39 (2006) 434-442). The absence of shoulder was necessarily due to the overwhelming contribution of the HAp peak, which indirectly confirms the coexistence of HAp and OCP. The presence of OCP is not surprising as it is a precursor phase of HAp in bone (N. J. Crane, et al, Bone 39 (2006) 434-442).

2-D mappings of the Raman peak intensity of CaP over mineralized scaffolds revealed massive CaP deposition allover the (CHI/BMP-2)$_3$-treated ENM scaffold, while much lower, similar amounts of CaP were deposited both in absence of LbL treatment, and when PLL was used instead of CHI (data not shown). These results support the promising promotive effect of CHI/BMP-2 LbL deposits on biomineralization. Moreover, the choice of the polycationic component of the deposits is of crucial importance. The remarkable potency of CHI-based treatments in terms of biomineralization might be due to better cell access to the surface-immobilized BMP-2, which must be facilitated by the open, plate-like morphology of (CHI/BMP-2)$_3$ deposits, while the compact morphology of (PLL/BMP-2)$_3$ deposits might limit cell access to the embedded growth factor (FIGS. 9A; 9B). Distinct morphologies can be explained by the low flexibility/high persistence length (6-12 nm) of chitosan (H. Cölfen, et al. Polym. 45 (2001) 373-383), limiting the interactions with BMP-2, while the high flexibility/low persistence length (2 nm) of PLL (D. A. Brant, et al, J. Am. Chem. Soc. 87 (1965) 2788-2800) allows optimized interactions with BMP-2.

The results show that according to the invention (i) an ENM implant enriched in BMP-2 and having a controlled size and thickness can be designed, (ii) bone formation can be induced in vitro.

---

The invention claimed is:

1. A biomaterial comprising
a nanofibrous scaffold made of polymers, and optionally living cells, wherein said nanofibrous scaffold is made of nanofibers having a diameter of about 50 nm to about 1,000 nm,
wherein said nanofibrous scaffold is coated with an interrupted coating with 3 to 12 layer pairs, each layer pair comprising a layer of polyanions and a layer of polycations,
wherein each of said 3 to 12 layer pairs is in the form of or comprised within multilayered droplets on fiber surfaces of said nanofibrous scaffold,
wherein at least one of the multilayered droplets incorporates therapeutic molecules, and
wherein the multilayered droplets form the interrupted coating on the fiber surfaces of the nanofibrous scaffold, said interrupted coating partially covering the fiber surfaces with space between at least some of the multilayered droplets.

2. The biomaterial according to claim 1, wherein said nanofibrous scaffold is made of poly(ε-caprolactone) or of collagen.

3. The biomaterial according to claim 1, wherein said therapeutic molecule is a growth factor selected from the group consisting of a bone morphogenetic protein (BMP), a transforming growth factor (TGF), a fibroblast growth factor (FGF), and a nucleic acid coding therefore.

4. The biomaterial according to claim 3, wherein said growth factor is bone morphogenetic protein 2 (BMP2) or bone morphogenetic protein 7 (BMP7).

5. The biomaterial according to claim 1, wherein said polycations are chitosan or polymers of lysine.

6. The biomaterial according to claim 1, wherein said polyanions are the therapeutic molecules.

7. The biomaterial according to claim 1, wherein said biomaterial includes said living cells, and said living cells comprise one or both of osteoblasts and chondrocytes.

8. The biomaterial according to claim 1, wherein said biomaterial includes said living cells, and said living cells are comprised within a hydrogel deposited on said nanofibrous scaffold.

9. The biomaterial according to claim 7, wherein said biomaterial comprises osteoblasts.

10. The biomaterial according to claim 7, wherein said biomaterial comprises chondrocytes that are comprised within an alginate hydrogel; and osteoblasts.

11. The biomaterial according to claim 1, wherein said biomaterial does not comprise living cells.

12. The biomaterial of claim 9, wherein said osteoblasts are comprised within a collagen hydrogel.

13. A method for producing a biomaterial comprising the steps of:
a) producing or obtaining a nanofibrous scaffold made of biodegradable polymers, wherein said nanofibrous scaffold is made of nanofibers having a diameter of about 50 nm to about 1,000 nm; and
b) coating said nanofibrous scaffold with an interrupted coating with 3 to 12 layer pairs, each layer pair comprising a layer of polyanions and a layer of polycations,
wherein each of said 3 to 12 layer pairs is in the form of or comprised within multilayered droplets on fiber surfaces of said nanofibrous scaffold,
wherein at least one of the multilayered droplets incorporates therapeutic molecules, and
wherein the multilayered droplets form the interrupted coating on the fiber surfaces of the nanofibrous scaffold, said interrupted coating partially covering the fiber surfaces with space between at least some of the multilayered droplets.

14. The method of claim 13, wherein said step of coating the nanofibrous scaffold comprises the steps of:
i. immersing the nanofibrous scaffold in a solution comprising the polycations;
ii. rinsing the nanofibrous scaffold obtained at the end of step (i);
iii. immersing the nanofibrous scaffold obtained at the end of step (ii) in a solution comprising the polyanions;
iv. rinsing the nanofibrous scaffold obtained at the end of step (iii); and, optionally,
v. repeating step (i) to (iv) for at least a second time; and, optionally,
vi. sterilizing the nanofibrous scaffold obtained at the end of step (iv) or (v).

15. A method for treating defective filling of one or both of bone and cartilage, or for regenerating one or both of bone and cartilage, comprising the step of
implanting in an individual in need thereof a biomaterial comprising
a nanofibrous scaffold, wherein said nanofibrous scaffold is made of nanofibers having a diameter of about 50 nm to about 1,000 nm,
wherein said nanofibrous scaffold is coated with an interrupted coating with 3 to 12 layer pairs, each layer pair comprising a layer of polyanions and a layer of polycations, and optionally with living cells,
wherein each of said 3 to 12 layer pairs is in the form of or comprised within multilayered droplets on fiber surfaces of said nanofibrous scaffold, wherein at least one of the multilayered droplets incorporates therapeutic molecules, and wherein the multilayered droplets form the interrupted coating on the fiber surfaces of the nanofibrous scaffold, said interrupted coating partially covering the fiber surfaces with space between at least some of the multilayered droplets.

16. A method for treating a one or both of a bone defect and a cartilage defect comprising the step of implanting in an individual in need thereof a biomaterial comprising a nanofibrous scaffold, wherein said nanofibrous scaffold is made of nanofibers having a diameter of about 50 nm to about 1,000 nm, wherein said nanofibrous scaffold is coated with an interrupted coating with 3 to 12 layer pairs, each layer pair comprising a layer of polyanions and a layer of polycations, and optionally with living cells, wherein each of said 3 to 12 layer pairs is in the form of or comprised within multilayered droplets on fiber surfaces of said nanofibrous scaffold, wherein at least one of the multilayered droplets incorporates therapeutic molecules, and wherein the multilayered droplets form the interrupted coating on the fiber surfaces of the nanofibrous scaffold, said interrupted coating partially covering the fiber surfaces with space between at least some of the multilayered droplets.

17. The method according to claim 16, wherein said individual suffers from a condition selected from the group consisting of: osteochondritis dissecans; osteonecrosis; osteochondral fracture(s); spinal fusion; a defect of one or both of bone and cartilage due to an injury; a defect of one or both of bone and cartilage due to ageing; a defect of one or both of bone and cartilage necessitating maxillofacial reconstruction, a defect of one or both of bone and cartilage necessitating sinus lift; a defect of one or both of bone and cartilage necessitating alveolar ridge augmentation; and a loss of one or both of bone and cartilage due to a tumor.

18. The method according to claim 16, wherein said biomaterial comprises said living cells, and wherein said living cells are osteoblasts.

19. The method of claim 16, wherein said individual suffers from a subchondral bone defect or an osteochondral defect and said biomaterial comprises said living cells, and wherein said living cells are one or both of osteoblasts and chondrocytes.

20. The method of claim 19, wherein said chondrocytes are comprised within an alginate hydrogel.

21. The method of claim 16, wherein said individual suffers from one or both of a small bone defect and a cartilage defect and wherein said biomaterial does not comprise living cells.

22. The method of claim 16, wherein said biomaterial comprises said living cells, and said living cells are isolated from the patient to be treated.

* * * * *

SEQUENCE LISTING

<160> NUMBER OF SEQ ID NOS: 2

<210> SEQ ID NO 1
<211> LENGTH: 115
<212> TYPE: PRT
<213> ORGANISM: Homo sapiens

<400> SEQUENCE: 1

```
Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Phe Pro Leu Ala Asp His Leu Asn Ser Thr Asn His Ala Ile Val
    50                  55                  60

Gln Thr Leu Val Asn Ser Val Asn Ser Lys Ile Pro Lys Ala Cys Cys
65                  70                  75                  80

Val Pro Thr Glu Leu Ser Ala Ile Ser Met Leu Tyr Leu Asp Glu Asn
                85                  90                  95
```

```
Glu Lys Val Val Leu Lys Asn Tyr Gln Asp Met Val Val Glu Gly Cys
                100                 105                 110

Gly Cys Arg
        115

<210> SEQ ID NO 2
<211> LENGTH: 431
<212> TYPE: PRT
<213> ORGANISM: Homo sapiens

<400> SEQUENCE: 2

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
                35                  40                  45

Gln Glu Arg Arg Glu Met Gln Arg Glu Ile Leu Ser Ile Leu Gly Leu
50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
                115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
                195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
                275                 280                 285

Arg Ser Ile Arg Ser Thr Gly Ser Lys Gln Arg Ser Gln Asn Arg Ser
                290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350
```

-continued

```
Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430
```